(12) United States Patent  
Kowari et al.

(10) Patent No.: US 8,105,535 B2  
(45) Date of Patent: Jan. 31, 2012

(54) PIPETTE TIP SUPPLIER, SAMPLE ANALYZER AND PIPETTE TIP SUPPLYING METHOD

(75) Inventors: Takeo Kowari, Kobe (JP); Takayoshi Izumi, Kobe (JP)

(73) Assignee: Sysmex Corporation, Kobe-Shi (JP)

( * ) Notice: Subject to any disclaimer, the term of this patent is extended or adjusted under 35 U.S.C. 154(b) by 604 days.

(21) Appl. No.: 12/212,008

(22) Filed: Sep. 17, 2008

(65) Prior Publication Data

US 2009/0078717 A1    Mar. 26, 2009

(30) Foreign Application Priority Data

Sep. 20, 2007   (JP) ................................. 2007-244008

(51) Int. Cl.
*G01N 35/10* (2006.01)
*G01N 35/04* (2006.01)
(52) U.S. Cl. ................ 422/65; 422/63; 422/66; 436/44; 436/47; 436/180; 221/163; 198/570
(58) Field of Classification Search .................. None
See application file for complete search history.

(56) References Cited

U.S. PATENT DOCUMENTS

2007/0148042 A1* 6/2007 Ootani et al. .................... 422/63
2007/0212260 A1* 9/2007 Fukuda et al. ................... 422/64
2007/0269342 A1* 11/2007 Kitagawa ......................... 422/64

FOREIGN PATENT DOCUMENTS

JP         2000-019182 A     1/2000

* cited by examiner

*Primary Examiner* — P. Kathryn Wright
(74) *Attorney, Agent, or Firm* — Sughrue Mion, PLLC

(57) ABSTRACT

The present invention is to present a pipette tip supplier which is capable of convey the pipette tip smoothly. The pipette tip supplier 30 comprises: container 31 for containing pipette tips 3; separator 36 for separating pipette tips one by one; transporting section 37 for transporting pipette tips separated by the separator 36, one by one, to a first position via a second position and for dropping the transported pipette tips from the first position, the pipette tips transported by the transporting section 37 comprising a preceding pipette tip and a following pipette tip transported after the preceding pipette tip; detector 40*e* for detecting the following pipette tip at the second position before the following pipette tip arrives at the first position; and controller 2*a* for controlling the transporting section 37 so as to suspend transporting operation when the detector 40*e* detects the following pipette tip at the second position.

14 Claims, 20 Drawing Sheets

PIPETTE TIP SUPPLIER, SAMPLE ANALYZER AND PIPETTE TIP SUPPLYING METHOD

FIELD OF THE INVENTION

The present invention relates to a pipette tip supplier, a sample analyzer, and a pipette tip supplying method, in particular, to a pipette tip supplier equipped with a transporting section for transporting pipette tips, a sample analyzer, and a pipette tip supplying method.

BACKGROUND

A sample analyzer equipped with a dispensing nozzle for aspirating and discharging liquid such as samples and reagents, in which a disposable pipette tip is detachably attached to the distal end of the dispensing nozzle to prevent contamination, is conventionally known. In such analyzers, a pipette tip supplier for supplying the pipette tip to the dispensing nozzle one by one so as to continuously perform the dispensing task is generally arranged.

As for such pipette tip supplier, Japanese Laid-Open Patent Publication No. 2000-19182 and the like has disclosed a pipette tip setting machine including a stocker containing the pipette tips; a bucket conveyor for sequentially conveying the pipette tips contained in the stocker to the upper side, and dropping the pipette tip conveyed to the upper side; a funnel shaped hopper to which the pipette tip dropped from the bucket conveyor is guided through a shoot; and a conveyance rail, disposed with the pipette tip guided by the hopper, for conveying the disposed pipette tip.

However, in the pipette tip supplier disclosed in Japanese Laid-Open Patent Publication No. 2000-19182, the pipette tip is sequentially dropped to the shoot by the bucket conveyor, and thus the pipette tips may accumulate in the shoot and the hopper in the path from the shoot to the hopper. In this case, the pipette tip may get stuck in the hopper or be disposed on the conveyance rail in an overlapping state, and may not be smoothly conveyed.

The present invention has been developed in view of the above aspects and is to present a pipette tip supplier which is capable of convey the pipette tip smoothly.

SUMMARY OF THE INVENTION

A first aspect of the present invention is a pipette tip supplier for supplying a pipette tip used in a dispensing device, comprising: a container for containing pipette tips; a separator for separating pipette tips supplied from the container one by one; a transporting section for transporting pipette tips separated by the separator, one by one, to a first position via a second position and for dropping the transported pipette tips from the first position, the pipette tips transported by the transporting section comprising a preceding pipette tip and a following pipette tip which is transported after the preceding pipette tip; a first detector for detecting the following pipette tip at the second position before the following pipette tip arrives at the first position; and a controller for controlling the transporting section so as to suspend transporting operation when the first detector detects the following pipette tip at the second position.

A second aspect of the present invention is a sample analyzer comprising: a container for containing pipette tips for dispensing samples; a separator for separating pipette tips supplied from the container one by one; a transporting section for transporting the pipette tips separated by the separator, one by one, to a first position via a second position and for dropping the transported pipette tips from the first position, the pipette tips transported by the transporting section comprising a preceding pipette tip and a following pipette tip which is transported after the preceding pipette tip; a first detector for detecting the following pipette tip at the second position before the following pipette tip arrives at the first position; a controller for controlling the transporting section so as to suspend transporting operation when the first detector detects the following pipette tip at the second position; a holder for holding a pipette tip dropped from the transporting section; a dispenser comprising an aspirating nozzle to which the pipette tip held by the holder is attachable, and for dispensing a sample with the pipette tip attached to the aspirating nozzle; and an analyzing section for analyzing the sample dispensed by the dispenser.

A third aspect of the present invention is a pipette tip supplying method for supplying a pipette tip used in a dispensing device, comprising steps of: (a) separating pipette tips supplied from a container containing pipette tips one by one; (b) transporting the pipette tips separated in step (a), one by one, toward a first position through a second position, the pipette tips transported in the step (b) comprising a preceding pipette tip and a following pipette tip which is transported after the preceding pipette tip; (c) detecting the following pipette tip at the second position before the following pipette tip arrives at the first position; (d) suspending transporting operation of the following pipette tip, when the following pipette tip is detected in step (c); and (e) resuming the suspended transporting operation to transport the second pipette tip detected in the step (c) to the first position, and dropping the following pipette tip from the first position.

DETAILED DESCRIPTION OF THE PREFERRED EMBODIMENTS

The preferred embodiments of the present invention will be described hereinafter with reference to the drawings.

A configuration of an immune analyzer equipped with the pipette tip supplier according to one embodiment of the present invention will be described with reference to FIGS. 1 to 20.

Figure 1:
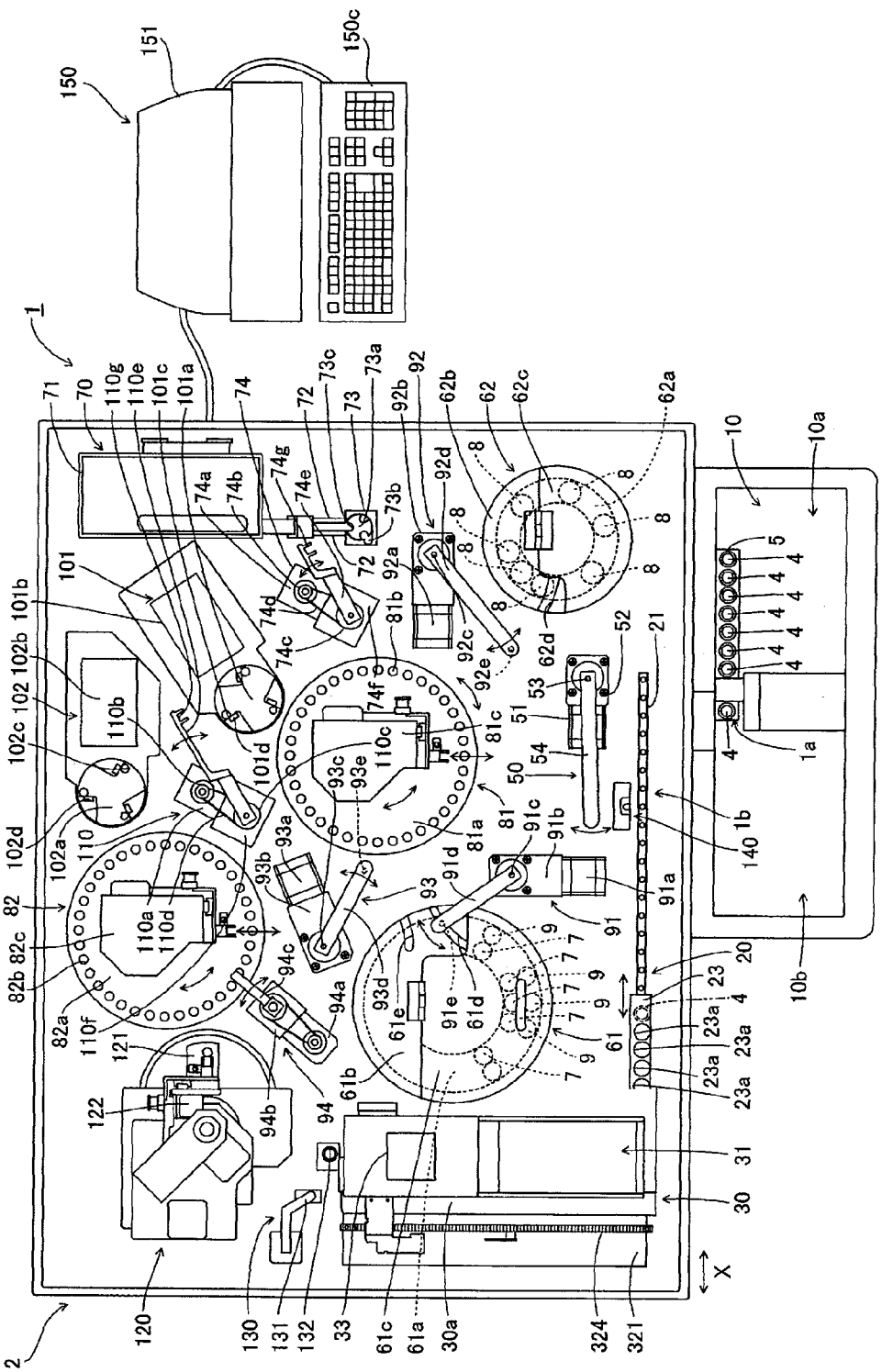
FIG. 1 is a plan view showing an overall configuration of an immune analyzer equipped with a pipette tip supplier according to one embodiment of the present invention.

An immune analyzer 1 equipped with a pipette tip supplier 30 according to one embodiment of the present invention is an apparatus for carrying out examinations on various items such as hepatitis B, hepatitis C, tumor marker, and thyroid hormone by using samples such as blood. As shown in FIG. 1, the immune analyzer 1 is configured by a measurement unit 2 having a function of measuring blood serving as a sample, and a data processing unit 150 for analyzing the measurement result output from the measurement unit 2 and obtaining an analysis result. The measurement unit 2 is configured by a sample conveyance section (sampler) 10, an urgent sample/tip conveyance section 20, a pipette supplier 30, a sample dispensing arm 50, reagent installing sections 61 and 62, a cuvette supply section 70, a primary reaction section 81 and a secondary reaction section 82, reagent dispensing arms 91, 92, 93, and 94, BF separators 101 and 102, a conveyance catcher section 110, a first detector 120, a waste section 130, and a tip detachment section 140. The immune analyzer 1 according to the present embodiment is configured to change the disposable pipette tip 3 (see FIG. 2) every time aspiration and discharge of the sample are carried out, in order to suppress samples such as blood aspirated and discharged by the sample dispensing arm 50 from mixing with other samples.

In the measurement unit 2 of the immune analyzer 1, magnetic particles (R2 reagent) are bonded to a trapped antibody (R1 reagent) bonded to an antigen or the measuring target to prepare a compound material of antigen-trapped antibody-magnetic particles, and thereafter, the compound material of antigen-trapped antibody-magnetic particles are attracted to a magnet 101$d$ of a BF (Bound Free) separator 101 to remove solution containing non-reactive (free) trapped antibody. The antigen of the compound material and a labeled antibody (R3 reagent) are bonded to prepare a compound material of antigen-trapped antibody-magnetic particles-labeled antibody, and thereafter, the compound material of antigen-trapped antibody-magnetic particles-labeled antibody are attracted to a magnet 102$d$ of a BF separator 102 to remove the R3 reagent containing non-reactive (free) labeled antibody. Furthermore, after adding a luminescent substrate (R5 reagent) that emits light in the reaction process with the labeled antibody, a light emission amount generated through the reaction of the labeled antibody and the luminescent substrate is measured. Through such processes, the antigen bound to the labeled antibody is quantitatively measured.

Figure 3:
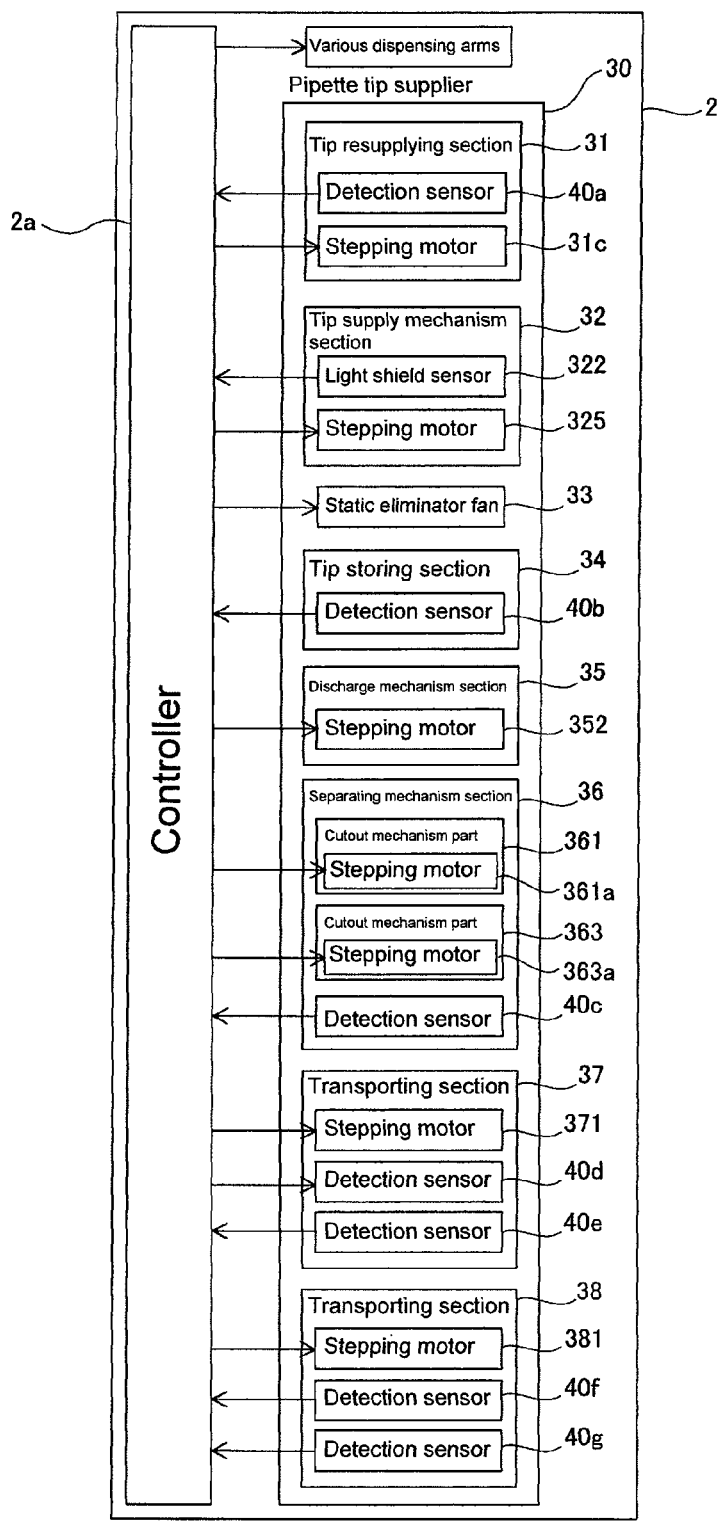
FIG. 3 is a block diagram showing a configuration of a measurement unit of the immune analyzer shown in FIG. 1.

As shown in FIG. 3, each mechanism (various dispensing arms, pipette tip supplier 30, and the like) in the measurement unit 2 are controlled by a controller 2$a$ arranged in the measurement unit 2. For instance, the controller 2$a$ receives signals of various sensors (detection sensors (transmissive sensors) 40$a$ to 40$g$ etc. to be hereinafter described) arranged in the pipette tip supplier 30, and controls the drive of various drive sources (stepping motor 361$a$, stepping motor 363$a$, and the like) arranged in the pipette tip supplier 30. The urgent sample/tip conveyance section 20 is also configured to be controlled by the controller 2$a$. Various dispensing arms, various sensors, and various drive sources will be described in detail below.

Figure 4:
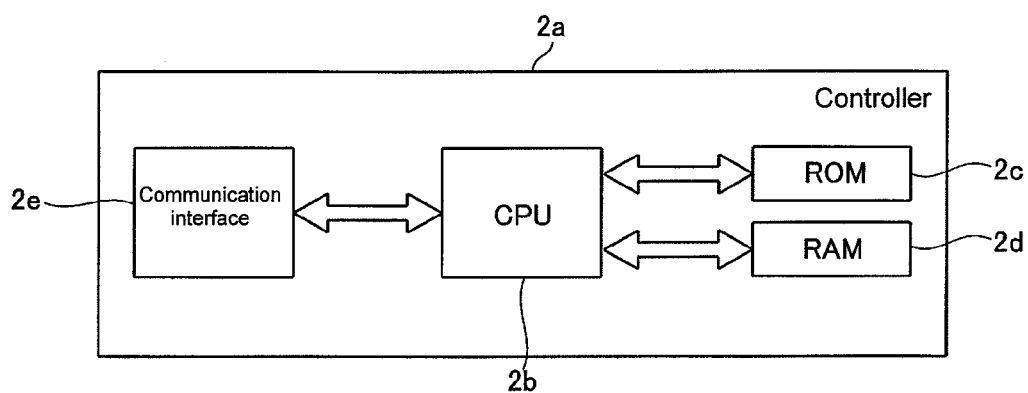
FIG. 4 is a block diagram showing a configuration of a controller of the measurement unit of the immune analyzer shown in FIG. 1.

As shown in FIG. 4, the controller 2$a$ is mainly configured by a CPU 2$b$, a ROM 2$c$, a RAM 2$d$, and a communication interface 2$e$.

The CPU 2$b$ can execute computer programs stored in the ROM 2$c$ and the computer programs read out into the RAM 2$d$. The ROM 2$c$ stores computer programs to be executed by the CPU 2$b$, data used to execute the computer programs, and the like. The RAM 2$d$ is used to read out the computer programs stored in the ROM 2$c$. The ROM 2$c$ is used as a work region of the CPU 2$b$ when executing these computer programs.

The communication interface 2$e$ is connected to the data processing unit 150 (see FIG. 1), and has a function of transmitting optical information (data of light emission amount generated by the reaction of the labeled antibody and the luminescent substrate) of the sample to the data processing unit 150, and receiving signals from a controller 150$a$, to be hereinafter described, of the data processing unit 150. The communication interface 2$e$ has a function of transmitting a command from the CPU 2$b$ to drive the urgent sample/tip conveyance section 200 (see FIG. 1) and each section of the measurement unit 2 (see FIG. 1).

As shown in FIG. 1, the sample conveyance section 10 is configured to convey a rack 5 mounted with a plurality of test tubes 4 containing the sample to a position corresponding to an aspirating position 1$a$ of the sample dispensing arm 50. The sample conveyance section 10 includes a rack set section 10$a$ for setting the rack 5 mounted with the test tube 4 containing un-processed sample, and a rack storing section 10$b$ for storing the rack 5 mounted with the test tube 4 containing dispense processed sample. The test tube 4 containing the un-processed sample is conveyed to the position corresponding to the aspirating position 1$a$ of the sample dispensing arm 50, the sample such as blood in the test tube 4 is aspirated by the sample dispensing arm 50, and the rack 5 mounted with the test tube 4 is stored in the rack storing section 10b.

Figure 5:
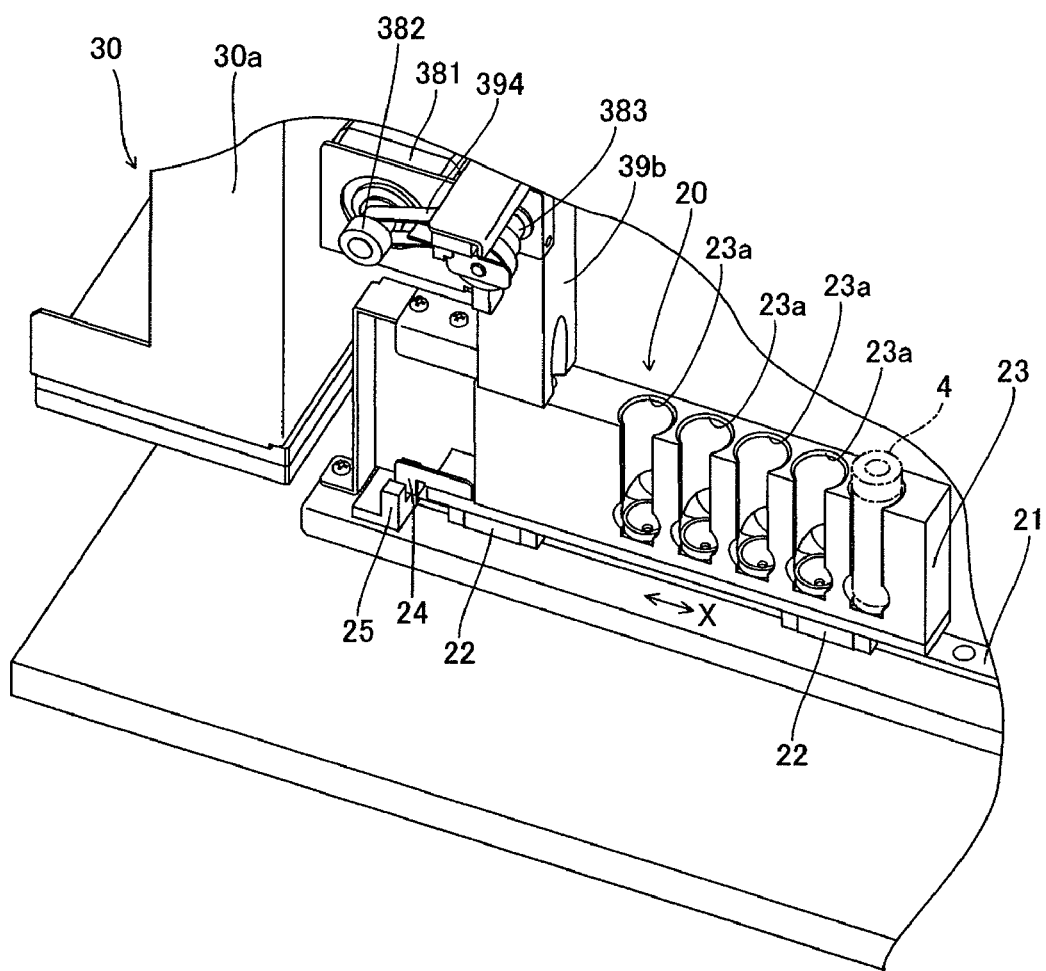
FIGS. 5 and 6 are perspective views showing an urgent sample conveyance section of the immune analyzer shown in FIG. 1.
Figure 6:
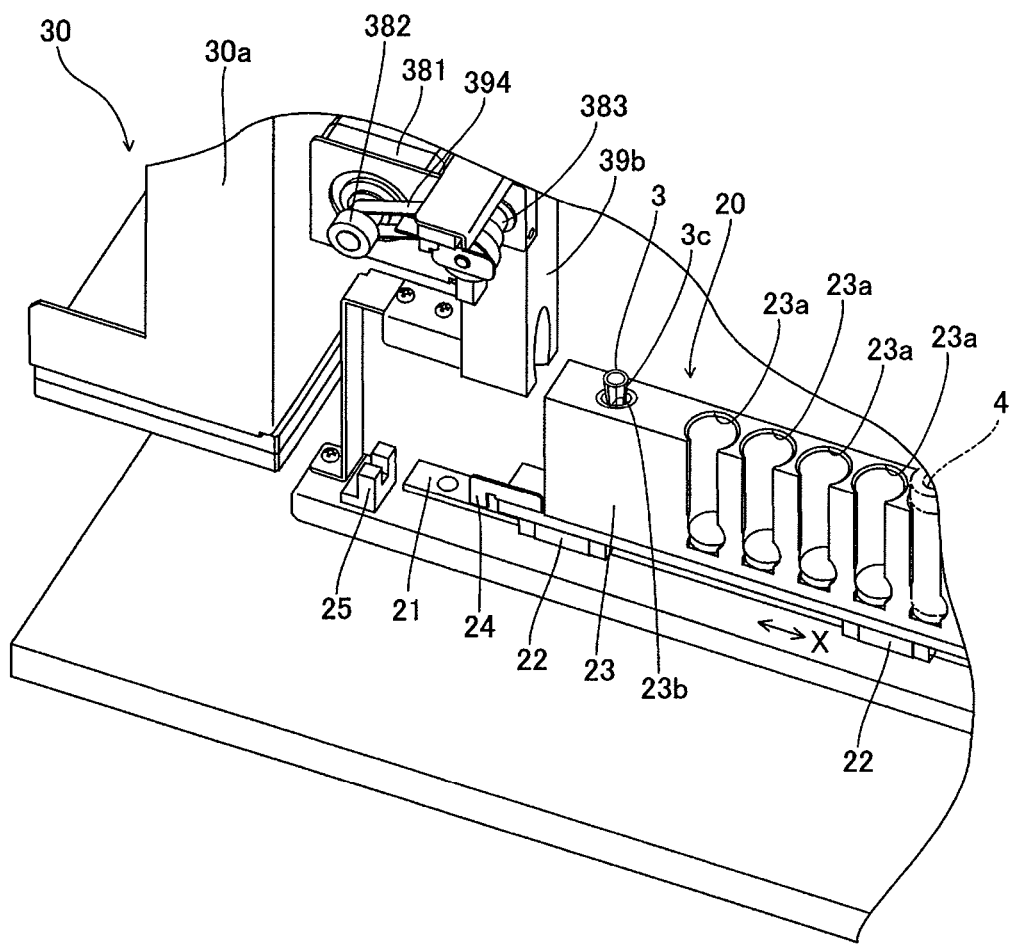

The urgent sample/tip conveyance section 20 is configured to convey the test tube 4, which contains urgent sample that needs to be cut into the sample being conveyed by the sample conveyance section 10 and examined, to an attachment position 1b of the sample dispensing arm 50. As shown in FIGS. 1, 5, and 6, the urgent sample/tip conveyance section 20 includes a slide rail 21 arranged extending in an X direction, a linear movement guide including a slide main body 22 moveably arranged along the slide rail 21, a conveyance rack 23 attached to the slide main body 22, a detection strip 24 attached to a lower part of the conveyance rack 23, and a light shield sensor 25 light shielded by the detection strip 24. The conveyance rack 23 is arranged with a test tube installing part 23a for mounting the test tube 4 containing the urgent sample, and a circular hole tip installing part 23b (see FIG. 6) for mounting the pipette tip 3 (see FIG. 2) supplied from the pipette tip supplier 30, to be hereinafter described. The detection strip 24 is arranged to light shield the light shield sensor 25 when arranged at a position of receiving the pipette tip 3 from the pipette tip supplier 30. The conveyance rack 23 is moved along the slide rail 21 by a driving force from a motor (not shown), so that the test tube 4 containing the urgent sample and the pipette tip 3 are conveyed to the attachment position 1b (see FIG. 1) of the sample dispensing arm 50.

Figure 7:
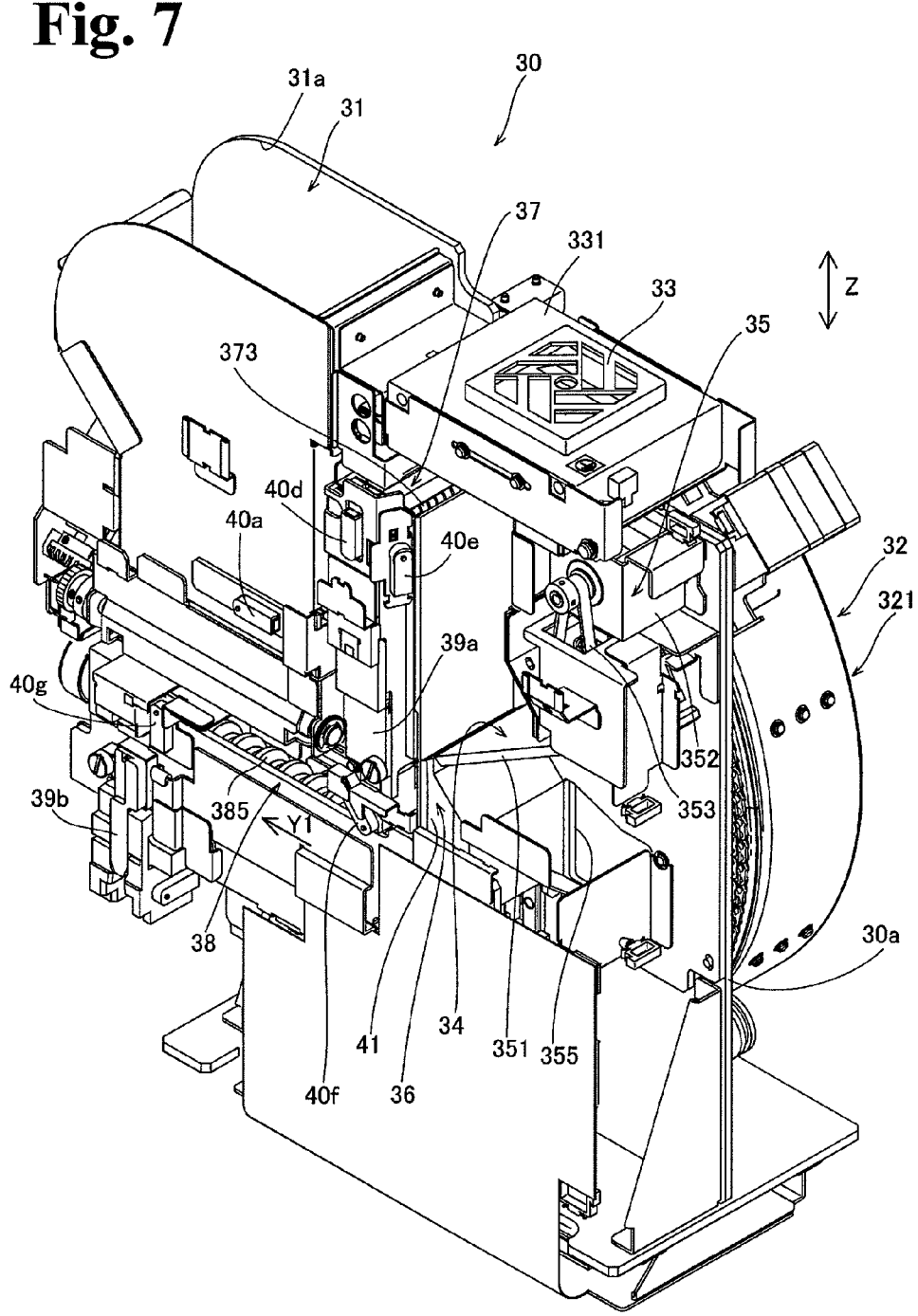
FIG. 7 is a perspective view showing an overall configuration of the pipette tip supplier according to one embodiment of the present invention.
Figure 8:
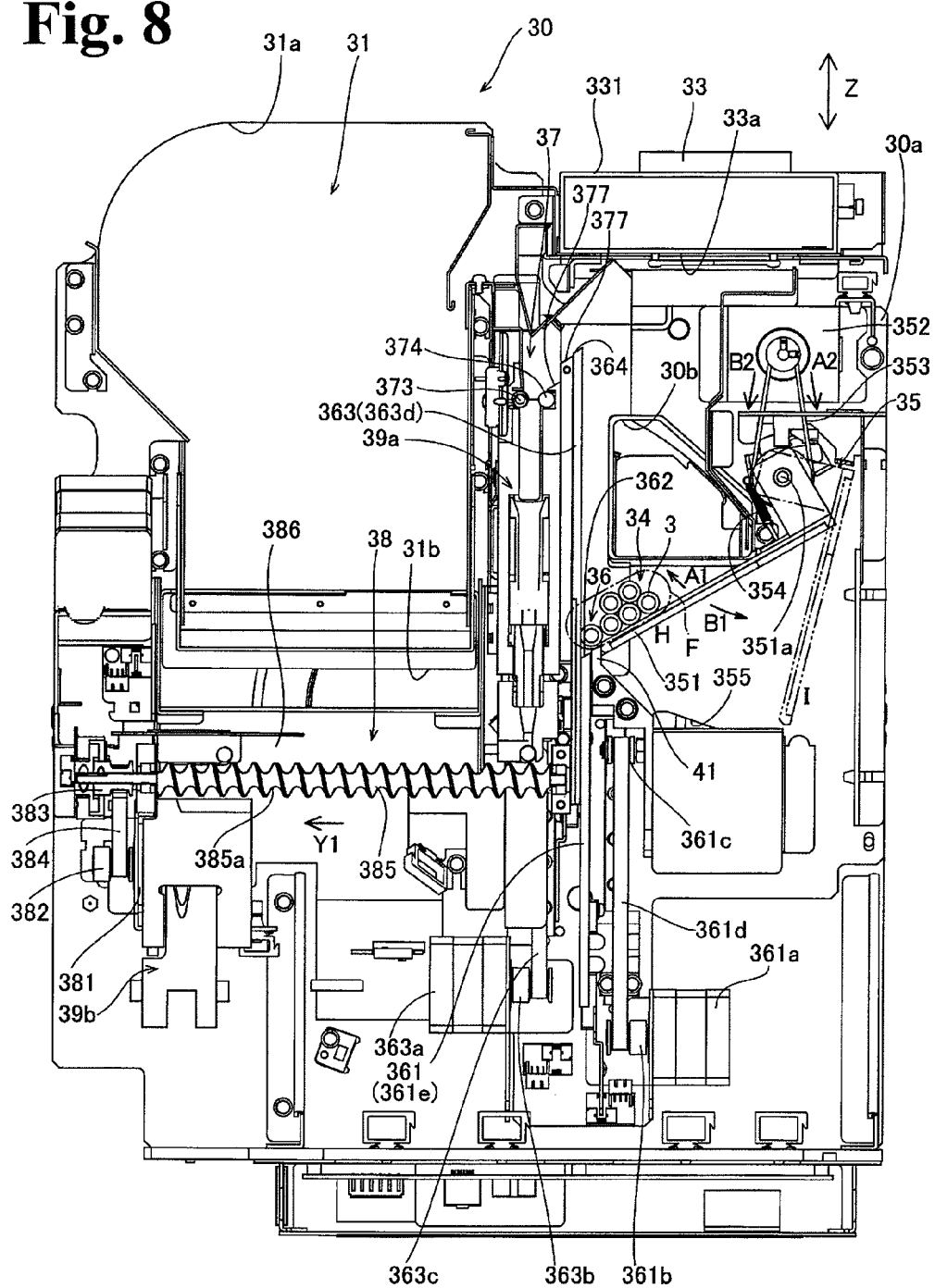
FIG. 8 is a cross sectional view showing an overall configuration of the pipette tip supplier according to one embodiment shown in FIG. 7.
Figure 9:
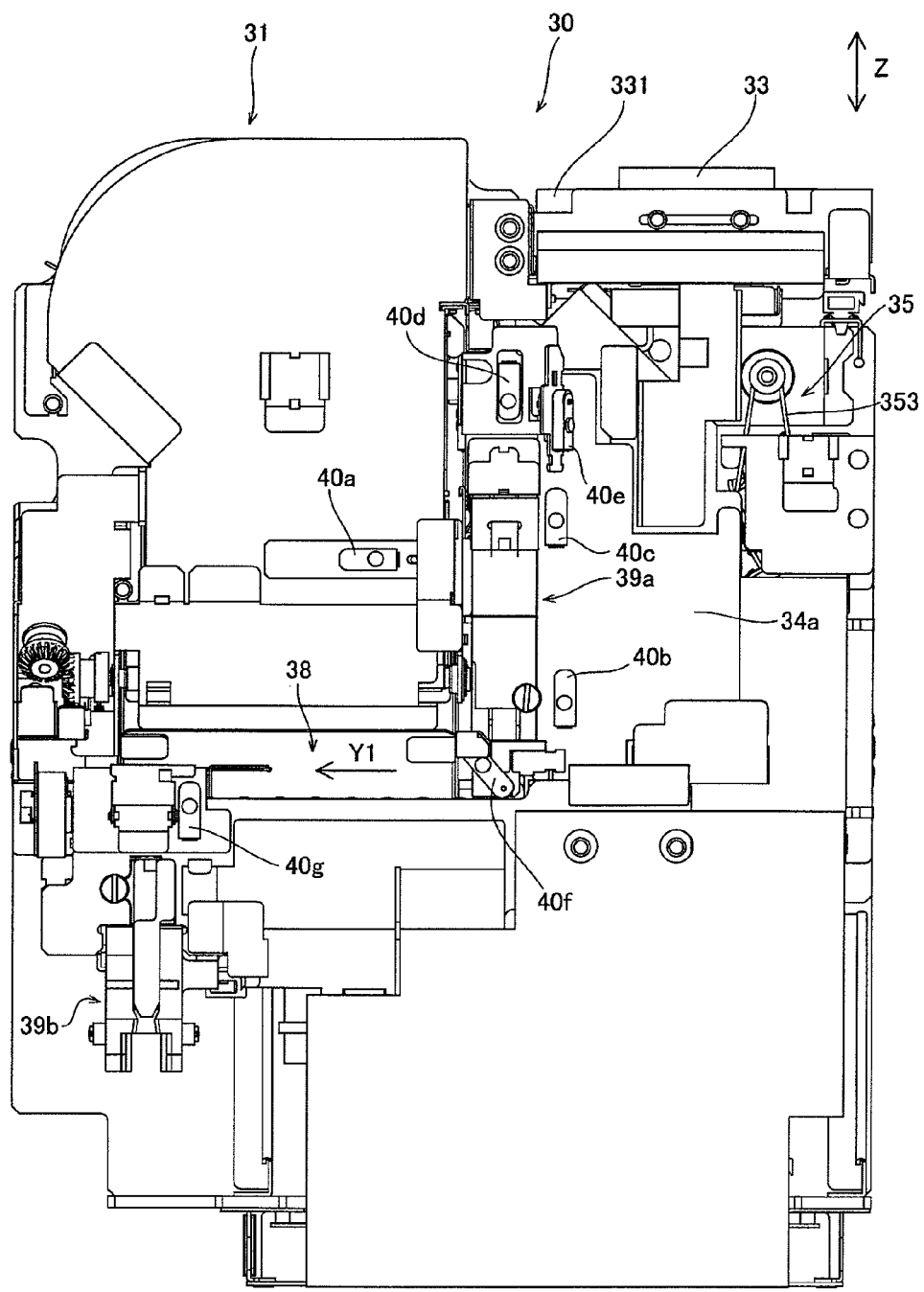
FIG. 9 is a front view showing an overall configuration of the pipette tip supplier according to one embodiment shown in FIG. 7.

In the present embodiment, the pipette tip supplier 30 has a function of disposing the pipette tip 3 (see FIG. 2) put into a tip resupplying section 31, to be hereinafter described, to the tip installing part 23b of the conveyance rack 23 of the urgent sample/tip conveyance section 20 one by one. The pipette tip supplier 30 also has a function of supplying the pipette tip to the tip installing part 23b of the conveyance rack 23 with the distal end 3a (see FIG. 2) of the pipette tip 3 directed downward. As shown in FIGS. 7 to 9, the pipette tip supplier 30 is configured by the tip resupplying section 31, a tip supply mechanism section 32, a static eliminator fan 33, a tip storing section 34, a discharge mechanism section 35, a separating mechanism section 36, a first transporting section 37 and a second transporting section 38, two shoots 39a and 39b, and seven detection sensors (transmissive sensors) 40a to 40g.

Figure 2:
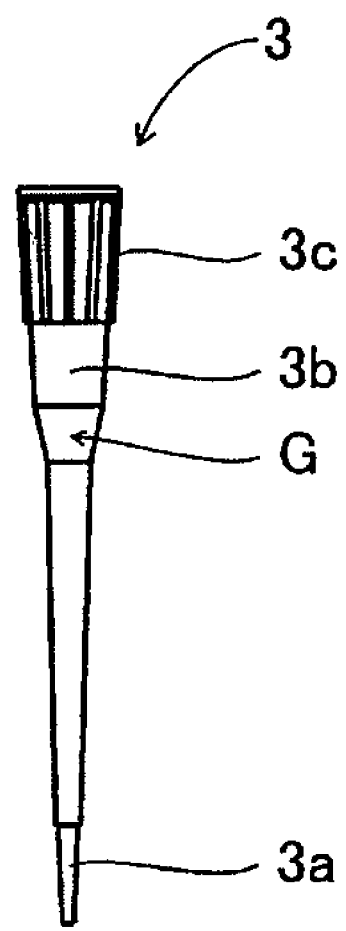
FIG. 2 is a front view of a pipette tip supplied by the pipette tip supplier according to one embodiment of the present invention.

The tip resupplying section 31 is configured to be able to contain a plurality of resupply pipette tips 3 (see FIG. 2). The pipette tip 3 contained in the tip resupplying section 30 is commercially available in a bag containing a plurality (e.g. 500) of pipette tips. The bagged pipette tips 3 tend to be charged with static electricity of about a few kV (e.g. about 6 kV) due to rubbing between the pipette tips 3 in the transport process of circulating in the market. As shown in FIG. 8, the tip resupplying section 31 includes an insert port 31a for inserting the plurality of pipette tips 3 taken out from the bag, and a discharge port 31b for discharging the contained pipette tip 3.

Figure 10:
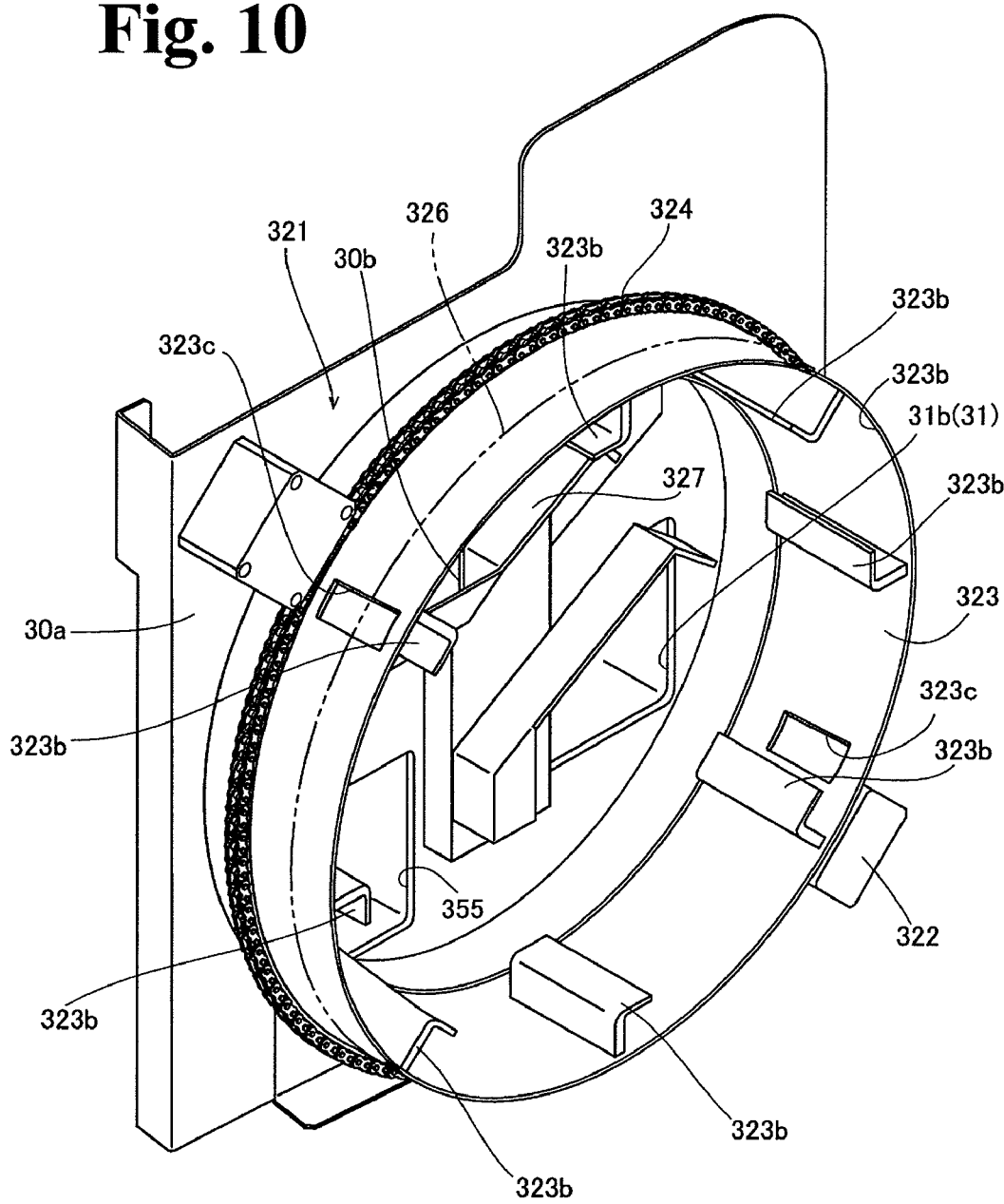
FIG. 10 is a perspective view of the pipette tip supplier according to one embodiment shown in FIG. 7 seen from a tip supply mechanism section side.

As shown in FIG. 10, the discharge port 31b of the tip resupplying section 31 is configured to guide the pipette tip 3 dropped from the discharge port 31b to a drum 323, to be hereinafter described, of the tip supply mechanism section 32. Specifically, a stepping motor 31c (see FIG. 3) for driving the discharge port 31b in an open/close manner is connected to the discharge port 31b. The stepping motor 31c drives the pipette tip 3 of the tip resupplying section 31 so as to be discharged from the discharge port 31b to the drum 323 of the drum part 321 when determined that the interior of the drum part 321 is not filled with the pipette tip 3 by the output of the light shield sensor 322 of the drum part 321 to be hereinafter described.

As shown in FIG. 9, a detection sensor (transmissive sensor) 40a for detecting the presence of the pipette tip 3 contained in the tip resupplying section 31 is arranged at a position in the position near the discharge port 31b of the tip resupplying section 31.

Figure 11:
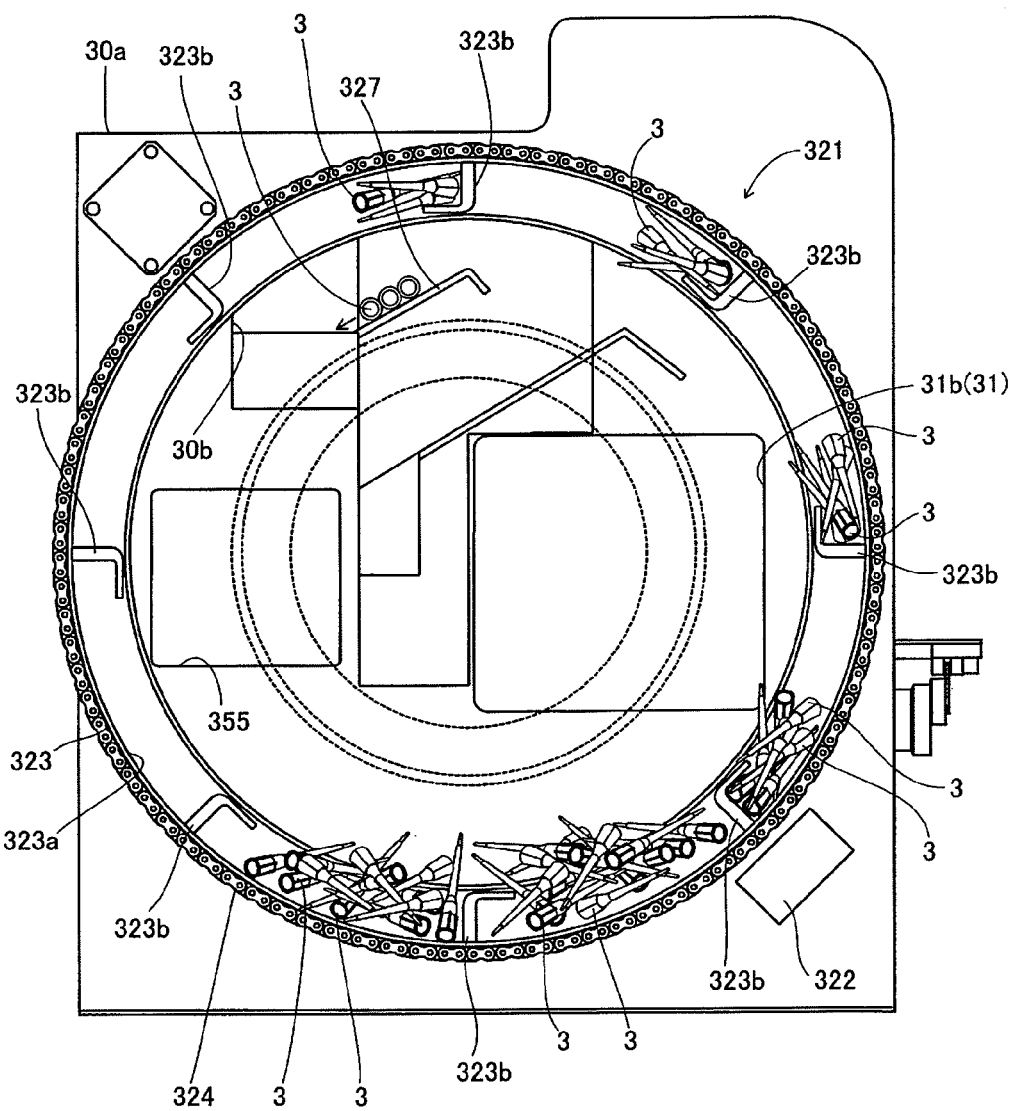
FIG. 11 is a from view of the pipette tip supplier according to one embodiment shown in FIG. 7 seen from the tip supply mechanism section side.

As shown in FIGS. 10 and 11, the tip supply mechanism section 32 has a function of receiving the pipette tip 3 inserted from the discharge port 31b of the tip resupplying section 31, and sending some of the received pipette tips 3 to the tip storing section 34. The tip supply mechanism section 32 is configured by a drum part 321 rotatably attached to a chassis 30a, and a light shield sensor 322 for detecting the rotation position of the drum part 321 and for detecting whether or not the interior of the drum part 321 is filled with the pipette tip 3. The drum part 321 includes a drum 323 of a tubular body capable of containing a plurality of pipette tips 3, a chain 324 wrapped around the outer circumference of the drum 323, a stepping motor 325 (see FIG. 3) for driving the chain 324, and a lid 326 (see FIG. 10) attached on the side opposite to the chassis 30a side so as to block a container 323a of the drum 323 of tubular body. A plurality of segmenting parts 323b capable of lifting the pipette tip 3 when the drum part 321 is rotated is arranged on the inner side of the drum 323. The segmenting part 323b has a shape such that the number of pipette tips 3 sent to the tip storing section 34 becomes a predetermined amount (three to five in the present embodiment), and is arranged so that excessive amount of pipette tip 3 is not sent to the tip storing section 34. Therefore, the ionized air blown from the static eliminator fan 33 uniformly hits the pipette tip 3 of the tip storing section 34 and effectively removes static electricity of the pipette tip.

The tip supply mechanism section 32 is arranged with a sending part 30b for sending the contained pipette tip 3, and the tip supply mechanism section 32 is configured so that the pipette tip 3 lifted by the segmenting part 323b is sent to the tip storing section 34 through the sending part 30b. A guide part 327 for receiving the pipette tip 3 dropped from the segmenting part 323b is arranged in the vicinity of the sending part 30b of the drum part 321, and the guide part 327 is configured so that the pipette tip 3 slides along the guide part 327 and is guided to the sending part 30b.

In the drum 323 of the drum part 321, two windows 323c made of polyvinyl chloride sheet are arranged at a spacing of 180 degrees. The two windows 323c are provided to be able to detect whether or not the pipette tip 3 is left inside the drum part 321 by the light shield sensor 322. Specifically, if the window 323c is covered with the pipette tip 3, the controller 2a determines that the pipette tip 3 is left inside the drum part 321, and if the window 323c is not covered with the pipette tip 3, the controller 2a determines that the pipette tip 3 is not left inside the drum part 321.

The chain 324 and the drum 323 wrapped with such chain 324 are rotated with the drive of the stepping motor 325 by configuring the drum part 321 as described above. The segmenting part 323b arranged on the inner side of the drum 323 also rotates with the rotation of the drum 323, and accompanied therewith, the pipette tip 3 stored at the lower part of the container 323a of the drum 323 is lifted by the segmenting part 323b, and sent to the tip storing section 34 to be hereinafter described through the sending part 30b (see FIG. 8) of the chassis 30a. As the pipette tips 3 contained inside the drum 323 rub against each other by the rotation of the drum 323, static electricity generates at the pipette tip 3.

As shown in FIGS. 7 and 8, the tip storing section 34 is configured by a region surrounded by the separating mechanism section 36, a receiving part 351 of the discharge mechanism section 35, the chassis 30a, and a cover member 34a (see FIG. 9). The tip storing section 34 is configured to store a predetermined amount of pipette tips 3 sent from the sending part 30b of the chassis 30a. The receiving part 351 is arranged so as to incline downward towards the separating mechanism section 36 side. The pipette tip 3 sent from the sending part 30b to the tip storing section 34 is placed on an inclined surface 362 of a cutout mechanism part 361 when the cutout mechanism part 361 of the separating mechanism section 36 to be hereinafter described is positioned at the lowermost point (position of FIG. 8). The static eliminator fan 33 is configured to blow ionized air to the separating mechanism section 36 side of the receiving part 351, wherein the ionized air uniformly hits the pipette tips 3, thereby effectively eliminating the electrification charges of the pipette tips 3.

The detection sensor (transmissive sensor) 40b (see FIG. 9) for detecting whether or not the pipette tip 3 is stored in the tip storing section 34 is arranged at the position near the separating mechanism section 36 of the receiving part 351. Specifically, the detection sensor 40b is attached to the cover member 34a (see FIG. 9), and is arranged to detect whether or not the pipette tip 3 to be placed is positioned on the inclined surface 362 of a movement member 361e of the cutout mechanism part 361 of the separating mechanism section 36 when the movement member 361e of the cutout mechanism part 361 of the separating mechanism section 36 to be hereinafter described is positioned on the lower side. When determined that the detection sensor 40b detects that the pipette tip 3 is not present on the inclined surface 362 of the movement member 361e of the cutout mechanism 361 (detection sensor 40b turned OFF) by the controller 2a, the tip supply mechanism section 32 is configured such that the stepping motor 325 is driven and the drum 323 is rotated. That is, the tip storing section 34 is supplied (sent) with the pipette tip 3 contained in the tip supply mechanism section 32 through the sending part 30b. When determined that the detection sensor 40b detects that the pipette tip 3 is present on the inclined surface 362 of the movement member 361e of the cutout mechanism part 361 (detection sensor 40b turned ON) by the controller 2a, the movement member 361e of the cutout mechanism part 361 is moved upward.

In the present embodiment, the static eliminator fan 33 has a function of blowing ionized air, and can perform an electricity removing operation of removing static electricity (electrification charge) of the pipette tip 3 stored in the tip storing section 34. As shown in FIGS. 7 and 8, the static eliminator fan 33 is arranged on the upper side of the tip storing section 34 and the sending part 30b so as not to contact the pipette tip 3, and is arranged on a lid 331 configured to be openable/closable. The lid 331 is arranged in an openable/closable manner to enable maintenance of the interior of the tip storing section 34 and to enable cleaning work of the static eliminator fan when drawbacks such as clogging of the pipette tip 3 arise inside the tip storing section 34. The lid 331 is configured to substantially close the space formed by the sending part 30b, the tip storing section 34, and the separating mechanism section 36. As shown in FIG. 8, the static eliminator fan 33 held by the lid 331 is arranged so that an air blow port 33a faces the vicinity of the separating mechanism section 36 side (region F of FIG. 8) of the receiving part 351. That is, the static eliminator fan 33 is arranged to blow ionized air to the pipette tip 3 positioned at the tip storing section 34, and blow ionized air to the pipette tip 3 positioned at the separating mechanism section 36. The static eliminator fan 33 is configured to be controlled by the controller 2a so that the drum 323 rotates, and the electricity removing operation of the pipette tip 3 starts in synchronization with the sending of the pipette tip 3 contained in the tip supply mechanism section 32 (drum 323) from the sending part 30b to the tip storing section 34.

As shown in FIGS. 7 and 8, the discharge mechanism section 35 is configured so that the receiving part 351 turns from a first position H shown in FIG. 8 to a second position I (open position) shown in FIG. 8. As shown in FIG. 8, the discharge mechanism section 35 is configured by the receiving part 351 configuring one part of the tip storing section 34, a stepping motor 352 or the drive source for driving the receiving part 351, a belt 353 for transmitting the driving force of the stepping motor 352 to the receiving part 351, and an extension coil spring 354 for holding the receiving part 351 at the chassis 30a.

The receiving part 351 is rotatably attached with a rotating shaft 351a as a center with respect to the chassis 30a. The other side of the extension coil spring 354 which one side is connected to the chassis 30a is connected to the receiving part 351. The extension coil spring 354 is arranged to bias the receiving part 351 in the A1 direction. The stepping motor 352 is attached to the chassis 30a. The belt 353 is configured so as to be moved in the A2 direction and the B2 direction by the stepping motor 352. The receiving part 351 is rotated in the A1 direction with the rotating shaft 351a as the center when the belt 353 is moved in the A2 direction, and rotated in the B1 direction with the rotating shaft 351a as the center when the belt 353 is moved in the B2 direction.

The discharge mechanism section 35 is configured to rotate the receiving part 351 in the B1 direction before the drum 323 is rotated to send the pipette tip 3 from the container 323a of the drum 323 to the tip storing section 34. The pipette tip 3 remaining in the tip storing section 34 is discharged to a tip return port 355. As shown in FIGS. 10 and 11, the tip return port 355 is connected to the container 323a of the drum 323, and the pipette tip 3 discharged to the tip return port 355 is returned to the container 323a. That is, the discharge mechanism section 35 is configured so as to be controlled to return the pipette tip 3 remaining in the tip storing section 34 to the container 323a when flowing in a new pipette tip 3 from the container 323a of the drum 323 to the tip storing section 34.

Figure 12:
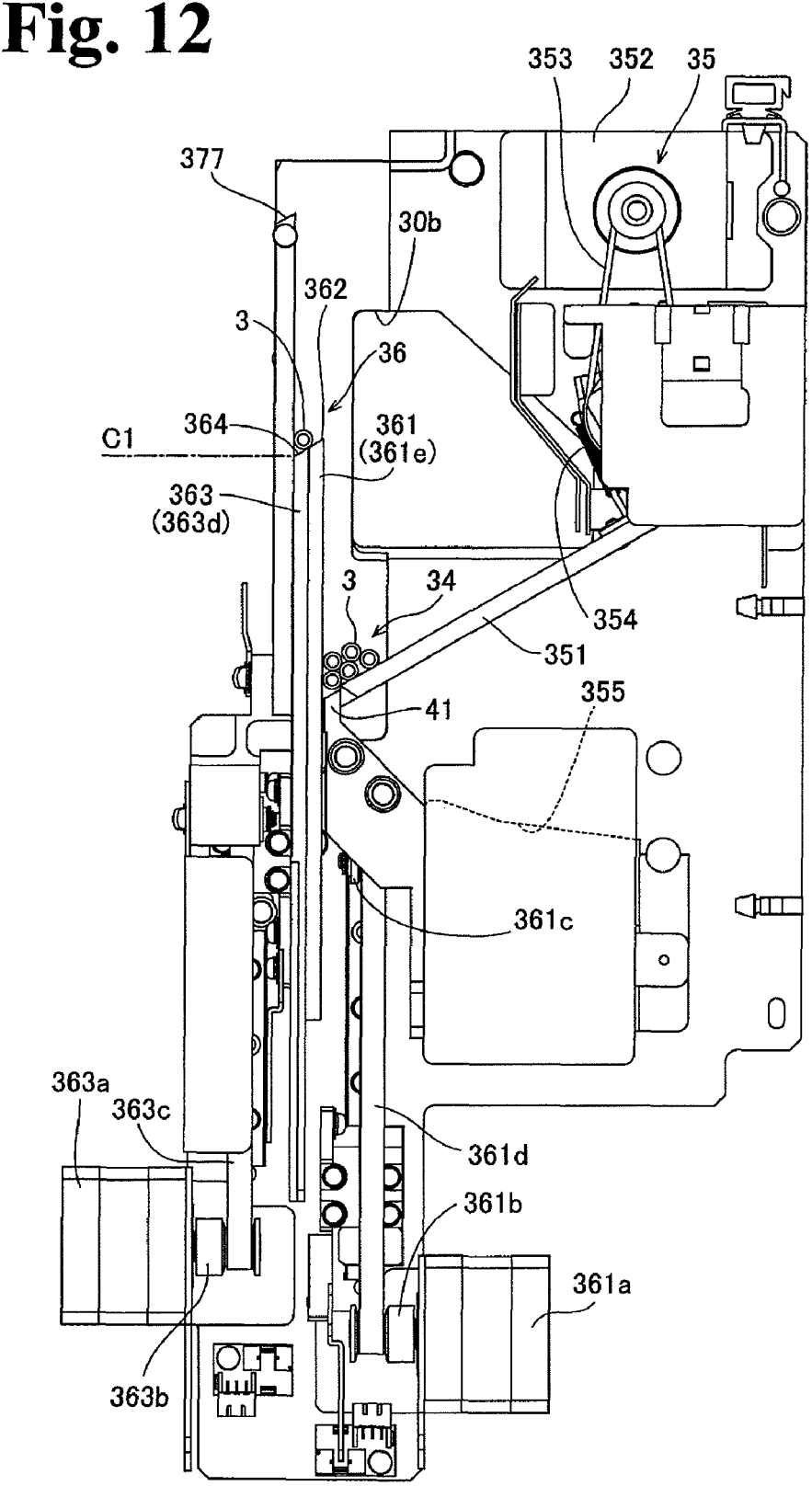
FIGS. 12 and 13 are views describing a structure of the periphery of a tip storing section and a separating mechanism section of the pipette tip supplier according to one embodiment shown in FIG. 7.
Figure 13:
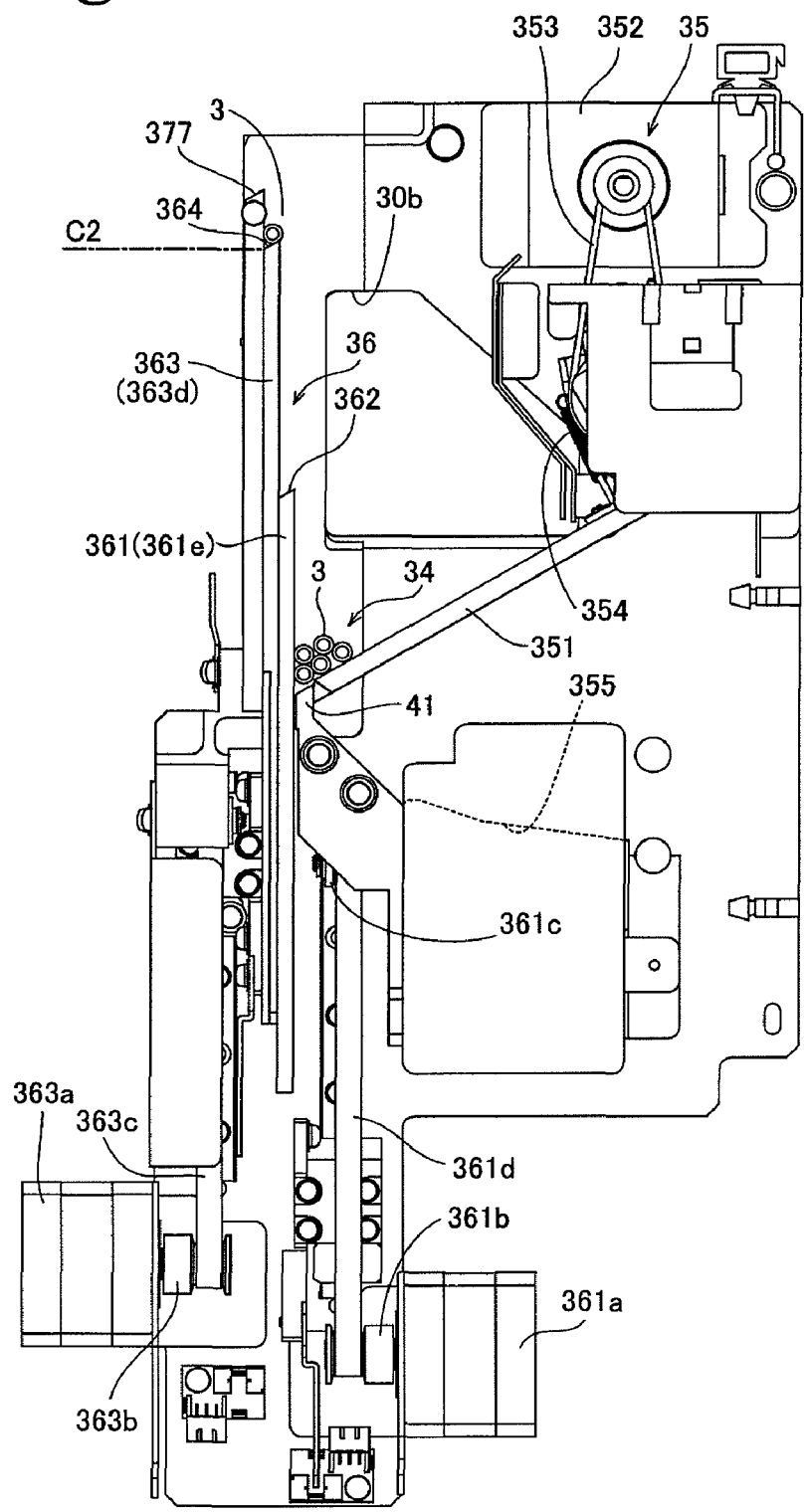

The separating mechanism section 36 is arranged to separate the pipette tips 3 received from the receiving part 351 through a relay member 41 one by one, and to send the pipette tip 3 separated one by one to the first transporting section 37. As shown in FIGS. 12 and 13, the separating mechanism section 36 includes the cutout mechanism part 361 for lifting the pipette tip 3 received from the receiving part 351 through the relay member 41 to the upper side, the inclined surface 362 for receiving the pipette tip 3 lifted by the cutout mechanism part 361 and guiding the same to the cutout mechanism part 363 to be hereinafter described, the cutout mechanism part 363 for lifting two or less pipette tips 3 received from the inclined surface 362 to the upper side, and an inclined surface 364 for receiving the pipette tip 3 lifted by the cutout mechanism part 363 and sending the same to the first transporting section 37.

The cutout mechanism part 361 is configured to separate one pipette tip 3 from the pipette tips 3 stored at least in plurals in the tip storing section 34. Specifically, as shown in FIG. 8, the cutout mechanism part 361 is configured by a stepping motor 361a serving as a drive source, a pulley 361b connected to the stepping motor 361a, a pulley 361c arranged at a predetermined spacing from the pulley 361b, a drive transmission belt 361d attached to the pulley 361b and the pulley 361c, and a movement member 361e coupled to the drive transmission belt 361d and movable in an up and down direction (Z-direction). When the stepping motor 361a is driven, the drive transmission belt 361*d* is driven by way of the pulley 361*b*, and thus the movement member 361*e* coupled to the drive transmission belt 361*d* is moved in the up and down direction (Z-direction). As a result, the pipette tips 3 placed on the inclined surface 362 are moved from a state (state of FIG. 8) in which the movement member 361*e* is positioned at the lowermost point to a state (state of FIG. 12) in which the movement member 361*e* is positioned at the uppermost point, and is sent to the inclined surface 364 of a state in which the movement member 363*d* is positioned at the lowermost point (state of C1 position of FIG. 12).

The movement member 361*e* of the cutout mechanism part 361 is configured to rise up to the vicinity (C1 position of FIG. 12) of the inclined surface 364 of the cutout mechanism part 363, and then rise little by little (by one pitch) in a step-wise manner at a predetermined time (about 0.3 sec) interval. According to such configuration, the pipette tip 3 positioned on the upper side rolls to the inclined surface 364 first even if the movement member 361*e* is raised with two pipette tips 3 mounted on the inclined surface 362 of the cutout mechanism part 361, and thus two pipette tips 3 can be suppressed from simultaneously rolling down the inclined surface 364.

The inclined surface 362 is configured by an inclined surface in which the pipette tip 3 can roll from the cutout mechanism part 361 side towards the cutout mechanism part 363 side.

The cutout mechanism part 363 has a function of sending (moving) the pipette tip 3 received from the inclined surface 362 to the first transporting section 37 one by one. Specifically, the cutout mechanism part 363 is configured by a stepping motor 363*a* serving as a drive source, a pulley 363*b* connected to the stepping motor 363*a*, a pulley (not shown) arranged at a predetermined spacing from the pulley 363*b*, a drive transmission belt 363*c* attached to the pulley 363*b* and the pulley (not shown), and a movement member 363*d* coupled to the drive transmission belt 363*d* and movable in the up and down direction (Z-direction). When the stepping motor 363*a* is driven, the drive transmission belt 363*c* is driven by way of the pulley 363*b*, and thus the movement member 363*d* coupled to the drive transmission belt 363*c* is moved in the up and down direction (Z-direction). As a result, the pipette tip 3 mounted on the inclined surface 364 of the movement member 363*d* can be lifted from C1 position of FIG. 12 to a C2 position of FIG. 13. In this case, the movement member 363*d* is formed to have a width such that only two or less pipette tips 3 can be mounted on the inclined surface 364. The movement member 363*d* is configured to be inclined such that even if moved upward (Z-direction) with two pipette tips 3 mounted on the inclined surface 364 of the movement member 363*d*, one of the two pipette tips 3 loses balance and drops to the inclined surface 362 side from the upper surface of the movement member 363*d*. Thus, even if two pipette tips 3 are mounted on the upper surface of the movement member 363*d*, the pipette tip 3 can be supplied to the first transporting section 37 one by one.

The movement member 363*d* of the cutout mechanism part 363 is configured to rise up to the vicinity (C2 position of FIG. 13) of the inclined surface 377 of the first transporting section 37, and then rise little by little (by one pitch) in a step-wise manner at a predetermined time (about 0.3 sec) interval. According to such configuration, the pipette tip 3 positioned on the upper side rolls to the inclined surface 377 first even if the movement member 363*d* is raised with two pipette tips 3 mounted on the inclined surface 364 of the cutout mechanism part 363, and thus two pipette tips 3 can be suppressed from simultaneously rolling down the inclined surface 377.

The separating mechanism section 36 and the static eliminator fan 33 are configured so that the electricity removing operation is stopped during at least one part of the period where the separating mechanism section 36 executes the separating operation by the controller 2*a*. Specifically, the static eliminator fan 33 is controlled by the controller 2*a* to interrupt the blow of ionized air during a period from a time point when the pipette tip 3 mounted on the inclined surface 364 of the movement member 363*d* of the cutout mechanism part 363 is moved to the vicinity (C2 position of FIG. 13) of the inclined surface 377 of the first transporting section 37 to a time point when the pipette tip 3 moved to the first transporting section 37 is detected by the detection sensor 40*d* to be hereinafter described. Thus, the balance of the pipette tip 3 can be suppressed from becoming unstable by the air blow of the static eliminator fan 33, and the pipette tip 3 can be suppressed from being moved to the first transporting section 37 in a balance different from the desired balance. When the detection sensor 40*d* to be hereinafter described detects the pipette tip 3, the static eliminator fan 33 is configured to be controlled by the controller 2*a* to resume air blow that has been interrupted.

The inclined surface 364 is configured to an inclined surface in which the pipette tip 3 can roll from the cutout mechanism part 363 side towards the inclined surface 377 side of the first transporting section 37, to be hereinafter described, and has a function of supplying the pipette tips 3 to the first transporting section 37.

The detection sensor (transmissive sensor) 40*c* (see FIG. 9) is attached to the cover member 34*a* (see FIG. 9), and is arranged to detect the presence of the pipette tip 3 mounted on the inclined surface 364 when the movement member 363*d* of the cutout mechanism part 363 is moved to the lower side (to position of C1 of FIG. 12). When the pipette tip 3 is not detected by the detection sensor 40*c* (detection sensor 40*c* is turned OFF), the cutout mechanism part 363 of the separating mechanism section 36 is prevented from operating. When the pipette tip 3 is detected by the detection sensor (transmissive sensor) 40*c* (detection sensor 40*c* is turned ON), the cutout mechanism part 363 of the separating mechanism section 36 is configured such that the movement member 363*d* is moved to the upper side (to position of C2 of FIG. 13).

Figure 14:
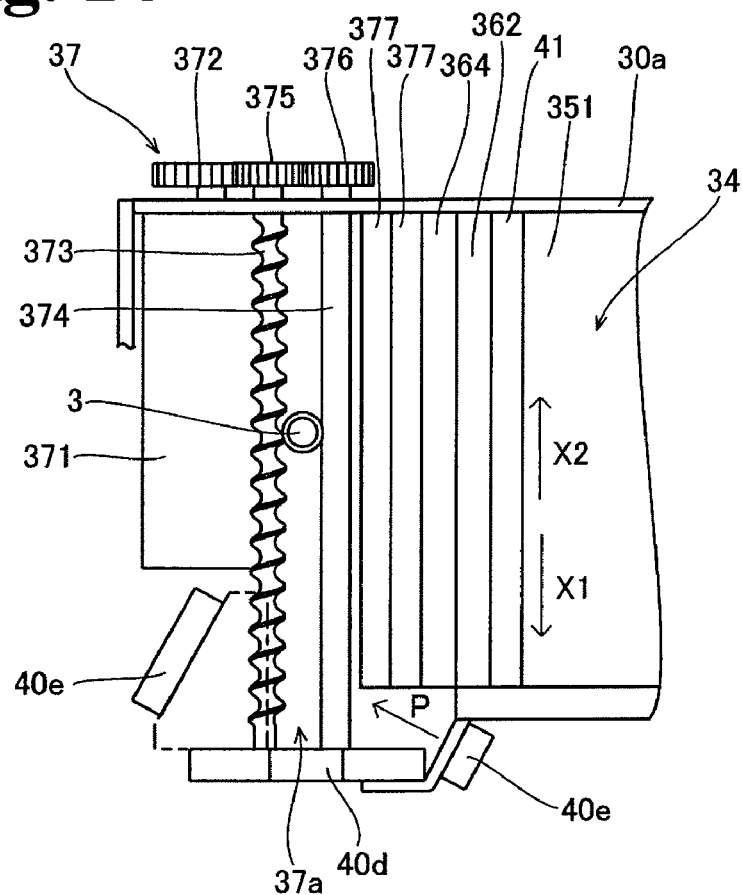
FIG. 14 is a plan view of a transporting section of the pipette tip supplier according to one embodiment shown in FIG. 7.
Figure 15:
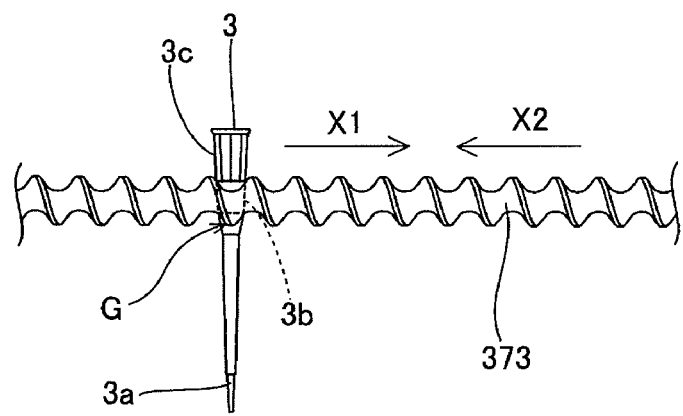
FIG. 15 is a side view of the transporting section of the pipette tip supplier according to one embodiment shown in FIG. 7.
Figure 16:
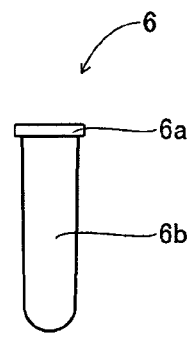
FIG. 16 is a front view of a cuvette used in the immune analyzer shown in FIG. 1.

The first transporting section 37 is arranged to move the pipette tip 3 separated one by one by the separating mechanism section 36 and rolled down from the inclined surface 364 of the separating mechanism section 36 in the direction of the arrow X1 (see FIG. 14). As shown in FIG. 14, the first transporting section 37 is configured by a stepping motor 371 serving as a drive source, a pulley 372 attached to the shaft of the stepping motor 371, a feeding screw 373, a shaft 374, a pulley 375 attached to the feeding screw 373 and connected to the pulley 372 by way of a belt (not shown), a pulley 376 attached to the shaft 374 and connected to the pulley 375 by way of a belt (not shown), and an inclined surface 377 for receiving the pipette tip 3 rolled down from the inclined surface 364 and for rolling the same to the shaft 374. The feeding screw 373 is rotatably attached with respect to the chassis 30*a*. The feeding screw 373 and the shaft 374 are arranged so as to extend parallel to each other with an interval being substantially the same as a diameter of a core 3*b* (see FIG. 2) of the pipette tip 3. The feeding screw 373 and the shaft 374 then can hold the core 3*b* of the pipette tip 3. In this case, as shown in FIG. 15, the core 3*b* of the pipette tip 3 held by the feeding screw 373 and the shaft 374 is positioned on the upper side than a center of gravity G (see FIG. 2) of the pipette tip 3, and thus is held by the feeding screw 373 and the shaft 374 with the distal end 3*a* of the pipette tip 3 rolled down from the inclined surface 364 of the separating mechanism section 36 facing downward. On the direction of the arrow X1 of the feeding screw 373 and the shaft 374, an insertion part 37a having a spacing larger than the diameter of an attachment part 3c of the pipette tip 3 is arranged when seen in plan view.

The detection sensor (transmissive sensor) 40d is arranged to detect whether or not the pipette tip 3 is held by the feeding screw 373 and the shaft 374. Specifically, the detection sensor 40d is arranged to emit light towards a direction (X direction) in which the feeding screw 373 extends, and is configured to detect whether or not the pipette tip 3 separated one by one by the separating mechanism section 36 is moved to the first transporting section 37 and the detection sensor 40d is turned ON. If the pipette tip 3 separated one by one by the separating mechanism section 36 is moved to the first transporting section 37 and the detection sensor 40d is turned ON, the controller 2a performs a control to move the feeding screw 373 in a reverse direction (direction of arrow X2) to the transporting direction of the pipette tip 3 by a first amount (about 10 mm). The distal end 3a of the pipette tip 3 thus fits between the screws of the feeding screws 373, the attachment part 3c engages with the feeding screw 373, and the pipette tip 3 is held by the feeding screw 373 and the shaft 374.

Furthermore, in the present embodiment, the detection sensor (transmissive sensor) 40e is arranged to emit light towards a direction of an arrow P of FIG. 14, and is configured to detect whether or not the pipette tip 3 is positioned at a suspended position before arriving at the insertion part 37a. That is, the detection sensor 40e is configured to detect whether or not the pipette tip 3 conveyed by the feeding screw 373 and the shaft 374 is sent to the suspended position in front of the insertion part 37a and the detection sensor 40e is turned ON.

In the present embodiment, if the pipette tip 3 is transported in the direction of the arrow X1 and the detection sensor 40e is turned ON when the pipette tip 3 is held by the feeding screw 373 and the shaft 374 and the detection sensor 40d is turned ON, the controller 2a is configured to stop the transportation of the pipette tip 3. When the detection sensor 40d is turned ON, if the pipette tip 3 is not detected at the position before arriving at the insertion part 37a by the detection sensor 40e after the feeding screw 373 of the first transporting section 37 carries out the transporting operation in the transporting direction (direction of arrow X1) of the pipette tip 3 by a second amount (about 100 mm), the controller 2a is configured to alternately execute the reverse transport control of transport operating the feeding screw 373 in a reverse direction (direction of arrow X2) to the transporting direction of the pipette tip 3 by the feeding screw 373 of the first transporting section 37 and a forward transport control of transporting operating the feeding screw 373 in the transporting direction (direction of arrow X1). This makes it possible that the distal end 3a of the pipette tip 3 then fits between the screws of the feeding screws 373, the attachment part 3c engages with the feeding screw 373, and the pipette tip 3 is easily held by the feeding screw 373 and the shaft 374.

In the present embodiment, the reverse transport control and the forward transport control are respectively repeatedly executed over second number of times N2 (fifteen times) until the pipette tip 3 is detected by the detection sensor 40e. After the first number of times N1 (fourth time and eighth time) of repeated execution over the second number of times N2 (fifteen times), the controller 2a is configured to execute the separating operation of separating the pipette tip 3 by the separating mechanism section 36 and supply the separated pipette tip 3 to the first transporting section 37. Accordingly, even if the distal end 3a of the pipette tip 3 is not fitted between the screws of the feeding screws 373, the new pipette tip 3 is supplied to the first transporting section 37, and the supplied pipette tip 3 is contacted to the pipette tip 3 previously arranged in the first transporting section 37, and thus the pipette tip 3 previously arranged in the first transporting section 37 can be easily held by the feeding screw 373 and the shaft 374.

In the present embodiment, after the reverse transport control and the forward transport control are repeatedly executed over the second number of times N2 (fifteen times), if the pipette tip 3 is not detected by the detection sensor 40e at the suspended position of before arriving at the insertion part 37a, the controller 2a outputs an error.

As shown in FIG. 8, the shoot 39a is arranged to guide the pipette tip 3 (see FIG. 2) dropped from the insertion part 37a (see FIG. 14) of the first transporting section 37 to the second transporting section 38.

The transporting section 38 is arranged to move the pipette tip 3 guided from the first transporting section 37 through the shoot 39a in the direction of the arrow Y1. The transporting section 38 is configured by a stepping motor 381 serving as a drive source (see FIG. 3), a pulley 382 attached to the stepping motor 381, a pulley 383 arranged at a predetermined spacing with the pulley 382, a drive transmission belt 384 attached to the pulley 382 and the pulley 383, and a feeding screw 385 rotatably placed with the rotation of the pulley 383. The feeding screw 385 has a groove 385a with a diameter smaller than the diameter of the attachment part 3c (see FIG. 2) of the pipette tip 3 and larger than the diameter of the core part 3b (see FIG. 2) of the pipette tip 3. A wall part 386 is arranged in parallel with a predetermined spacing with respect to the feeding screw 385 so that the pipette tip 3 fitted to the groove 385a of the feeding screw 385 does not drop. The feeding screw 385 and the wall part 386 then can hold the core part 3b of the pipette tip 3.

The detection sensor (transmissive sensor) 40f (see FIG. 9) is arranged near the lowermost portion of the shoot 39a, and is arranged to detect whether or not the pipette tip 3 guided from the first transporting section 37 through the shoot 39a has arrived the second transporting section 38. The detection sensor 40f is turned ON when the pipette tip 3 is positioned at the second transporting section 38 on the lower side of the shoot 39a, and is turned OFF when the pipette tip 3 is moved in the direction of the arrow Y1 by the second transporting section 38. The detection sensor (transmissive sensor) 40g (see FIG. 9) is arranged to detect whether or not the pipette tip 3 conveyed by the second transporting section 38 is conveyed up to immediately before being dropped to the shoot 39b.

In the present embodiment, when the pipette tip 3 held by the second transporting section 38 is transported in the direction of the arrow Y1, and the detection sensor 40f is turned OFF, the controller 2a performs a control to move the feeding screw 373 of the first transporting section 37, where transporting operation has been stopped, in the transporting direction (direction of arrow X1) of the pipette tip 3 by a first amount (about 10 mm). Since the pipette tip 3 held at the first transporting section 37 is dropped after the pipette tip 3 positioned at the lower side of the shoot 39a of the second transporting section 38 is transported, the pipette tips 3 can be suppressed from overlapping each other at the second transporting section 38.

In the present embodiment, after the feeding screw 373 of the first transporting section 37 where transporting operation has been stopped is moved in the transporting direction (direction of arrow X1) of the pipette tip 3 by the first amount (about 10 mm), and the operation of dropping the pipette tip 3 from the inserting part 37a is performed, if the detection sensor 40f does not detect the pipette tip 3, the controller 2a alternately executes the forward transport control of transport operating the feeding screw 373 of the first transporting section 37 in the transporting direction (direction of arrow X1) of the pipette tip 3, and the reverse transport control of transport operating the feeding screw 373 in a reverse direction (direction of arrow X2) to the transporting direction. The distal end 3a of the pipette tip 3 then easily fits between the screws of the feeding screws 373. Consequently, the attachment part 3c of the pipette tip 3 engages with the feeding screw 373, and the pipette tip 3 can be expected to be easily held by the feeding screw 373 and the shaft 374. It is also expected that the pipette tip 3 caught at the feeding screw 373 or the shaft 374 and thus not dropped can be dropped.

In the present embodiment, the forward transport control and the reverse transport control are respectively repeatedly executed over fourth number of times N4 (fifteen times) until the pipette tip 3 is detected by the detection sensor 40e when the pipette tip 3 is not detected by the detection sensor 40f. After the third number of times N3 (fifth time and tenth time) of repeated execution over the fourth number of times N4 (fifteen times), the controller 2a is configured to execute the separating operation of separating the pipette tip 3 by the separating mechanism section 36 and supply the separated pipette tip 3 to the first transporting section 37. Accordingly, even if the distal end 3a of the pipette tip 3 is not fitted between the screws of the feeding screws 373, the pipette tip 3 is newly supplied to the first transporting section 37, and the supplied pipette tip 3 is contacted to the pipette tip 3 previously arranged in the first transporting section 37, and thus the pipette tip 3 previously arranged in the first transporting section 37 can be easily held by the feeding screw 373 and the shaft 374.

In the present embodiment, when the pipette tip 3 is not detected by the detection sensor 40f, after the reverse transport control and the forward transport control are repeatedly executed over the fourth number of times N4 (fifteen times), if the pipette tip 3 is not detected at the position of before arriving at the insertion part 37a, the controller 2a outputs an error.

The shoot 39b is arranged to guide the pipette tip 3 conveyed by the second transporting section 38 to the tip installing part 23b of the conveyance rack 23 of the urgent sample/tip conveyance section 20 described above. The shoot 39b is formed so that the distal end 3a of the pipette tip 3 passing through slidably drops in an inclined state.

Figure 17:
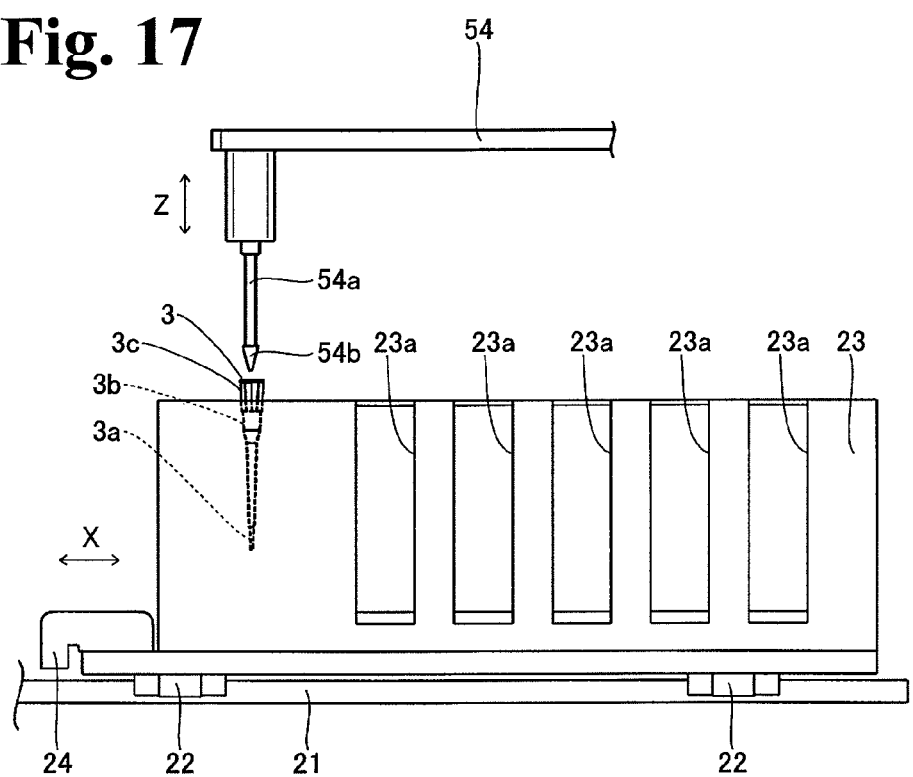
FIG. 17 is a side view of an urgent sample conveyance section and sample dispensing arm of the immune analyzer shown in FIG. 1.

The sample dispensing arm 50 has a function of dispensing the sample in the test tube 4 conveyed to the aspirating position 1a (see FIG. 1) by the sample conveyance section 10 or the sample in the test tube 4 conveyed to the attachment position 1b (see FIG. 1) by the urgent sample/tip conveyance section 20 into a cuvette 6 (see FIG. 16) held by a holder 81b of a rotatable table 81a of the primary reaction section 81 to be hereinafter described. As shown in FIGS. 1 and 17, the sample dispensing arm 50 includes a motor 51, a drive transmitting part 52 connected to the motor 51, and an arm 54 attached to the drive transmitting part 52 by way of a shaft 53. The drive transmitting part 52 is configured to turn the arm 54 with the shaft 53 as the center by the driving force from the motor 51, and move the arm in the up and down direction (Z direction). A nozzle 54a for aspirating and discharging the sample is arranged at the distal end of the arm 54. The pipette tip 3 conveyed by the conveyance rack 23 of the urgent sample/tip conveyance section 20 is attached to the distal end 54b of the nozzle 54a.

The reagent installing section 61 (see FIG. 1) includes an installing part 61a for installing a reagent bin 7 containing the R1 reagent including trapped antibody and a reagent bin 9 containing the R3 reagent including labeled antibody; an upper surface 61b arranged on the upper part of the installing part 61a so that foreign substances such as dust does not enter the R1 reagent in the reagent bin 7 or the R3 reagent in the reagent bin 9 installed in the installing part 61a; and a lid 61c attached in an openable/closable manner to the upper surface 61b. A groove 61d to be inserted with a nozzle 91e of the reagent dispensing arm 91, to be hereinafter described, and a groove 61e to be inserted with a nozzle 93e of the reagent dispensing arm 93 are formed in the upper surface 61b. The installing part 61a is rotatably configured to convey the installed reagent bin 7 and the reagent bin 9 to positions corresponding to the groove 61d and the groove 61e of the upper surface 61b, respectively.

The reagent installing section 62 (see FIG. 1) includes an installing part 62a for installing a reagent bin 8 containing the R2 reagent including magnetic particles; an upper surface 62b arranged on the upper part of the installing part 62a so that foreign substances such as dust do not enter the R2 reagent in the reagent bin 8 installed in the installing part 62a; and a lid 62c attached in an openable/closable manner to the upper surface 62b. A groove 62d to be inserted with a nozzle 92e of the reagent dispensing arm 92, to be hereinafter described, is formed in the upper surface 62b. The installing part 62a is rotatably configured to convey the installed reagent bin 8 to a position corresponding to the groove 62d of the upper surface 62b.

The cuvette supply section 70 (see FIG. 1) is configured so as to sequentially supply a plurality of cuvettes 6 (see FIG. 16) to the holder 81b of the rotatable table 81a of the primary reaction section 81. The cuvette supply section 70 includes a hopper 71 capable of containing the plurality of cuvettes 6, two inductive plates 72 arranged on the lower side of the hopper 71, a supporting board 73 arranged on the lower end of the inductive plate 72, and a supply catcher section 74. The two inductive plates 72 are arranged in parallel to each other at a spacing smaller than the diameter of a collar 6a (see FIG. 16) of the cuvette 6 and larger than the diameter of a core part 6b (see FIG. 16) of the cuvette 6. The plurality of cuvettes 6 supplied to the hopper 71 are arrayed along the inductive plate 72 with the collar 6a engaged to the upper surface of the two inductive plates 72 by applying vibration to the hopper 71. The supporting board 73 includes a rotatable part 73a rotatably arranged with respect to the supporting board 73 and a concave part 73b arranged to be adjacent to the rotatable part 73a. Three cutouts 73c are formed every predetermined angle (120° in the present embodiment) at the outer peripheral portion of the rotatable part 73a. The cutout 73c is arranged to contain the cuvette 6 induced by the inductive plate 72 one by one. The concave part 73b is configured so as to receive the cuvette 6 which rotates while being contained in the cutout 73c of the rotatable part 73a.

The supply catcher section 74 (see FIG. 1) has a function of transporting the cuvette 6 received by the concave part 73b to the holder 81b of the rotatable table 81a of the primary reaction section 81. The supply catcher section 74 includes a motor 74a, a pulley 74b connected to the motor 74a, a pulley 74c arranged with a predetermined spacing from the pulley 74b, a drive transmission belt 74d attached to the pulley 74b and the pulley 74c, an arm 74e attached to the pulley 74c by way of a shaft, and a drive part 74f for moving the arm 74e in the up and down direction (Z direction). A chuck part 74g for sandwiching and gripping the cuvette 6 is arranged at the distal end of the arm 74e.

The primary reaction section 81 (see FIG. 1) is arranged to rotatably transport the cuvette 6 held at the holder 81b of the rotatable table 81a by a predetermined angle for every predetermined period (18 seconds in the present embodiment), and to stir the sample, the R1 reagent, and the R2 reagent in the cuvette 6. The primary reaction section 81 is configured by the rotatable table 81a for conveying the cuvette 6 containing the sample, the R1 reagent, and the R2 reagent in the rotating direction, and a conveyance mechanism section 81c for stirring the sample, the R1 reagent, and the R2 reagent in the cuvette 6 and conveying the cuvette 6 containing the stirred sample, the R1 reagent, and the R2 reagent to the BF separator 101 to be hereinafter described.

The reagent dispensing arm 91 (see FIG. 1) has a function of aspirating the R1 reagent in the reagent bin 7 installed in the installing part 61a of the reagent installing section 61, and dispensing the aspirated R1 reagent into the cuvette 6 dispensed with the sample of the holder 81b of the rotatable table 81a of the primary reaction section 81. The reagent dispensing arm 91 includes a motor 91a, a drive transmitting part 91b connected to the motor 91a, and an arm 91d attached to the drive transmitting part 91b by way of a shaft 91c. The drive transmitting part 91b is configured so as to turn the arm 91d with the shaft 91c as the center by the driving force from the motor 91a, and move the arm in the up and down direction (Z-direction). A nozzle 91e for aspirating and discharging the R1 reagent in the reagent bin 7 is attached to the distal end of the arm 91d. That is, the nozzle 91e is configured so as to aspirate the R1 reagent in the reagent bin 7 by way of the groove 61d of the upper surface 61b of the reagent installing section 61, and thereafter, dispense the aspirated R1 reagent into the cuvette 6 dispensed with the sample.

The reagent dispensing arm 92 (see FIG. 1) has a function of dispensing the R2 reagent in the reagent bin 8 installed in the installing section 62a of the reagent installing section 62 into the cuvette 6 dispensed with the sample and the R1 reagent of the primary reaction section 81. The reagent dispensing arm 92 includes a motor 92a, a drive transmitting part 92b connected to the motor 92a, and an arm 92d attached to the drive transmitting part 92b by way of a shaft 92c. The drive transmitting part 92b is configured so as to turn the arm 92d by the driving force from the motor 92a with the shaft 92c as the center, and move the arm in the up and down direction (Z-direction). A nozzle 92e for aspirating and discharging the R2 reagent in the reagent bin 8 is attached to the distal end of the arm 92d. Therefore, the nozzle 92e is configured so as to aspirate the R2 reagent in the reagent bin 8 by way of the groove 62d of the upper surface 62b of the reagent installing section 62, and thereafter, dispense the aspirated R2 reagent into the cuvette 6 dispensed with the sample and the R1 reagent.

The BF (Bound Free) separator 101 (see FIG. 1) is arranged to remove the non-reactive R1 reagent in the cuvette 6 (see FIG. 16) received from the conveyance mechanism section 81c of the primary reaction section 81. The BF separator 101 includes an installing section 101a for installing the cuvette 6 and conveying the cuvette 6 in the rotating direction, and a separation stirring section 101b for aspirating the non-reactive R1 reagent. The installing section 101a includes three installing holes 101c for holding the cuvette 6, and a magnet 101d respectively arranged at the side of the three installing holes 101c. Thus, the bound antigen, the trapped antibody, and the magnetic particles in the cuvette 6 installed in the installing hole 101c can be attracted to the magnet 101d side. The sample or the like in the cuvette 6 is aspirated with the separation stirring section 101d in the attracted state to remove the non-reactive (free) R1 reagent not bound with the magnetic particles.

The conveyance catcher section 110 (see FIG. 1) has a function of conveying the cuvette 6 (see FIG. 16) of the installing section 101a of the BF separator 101 in which non-reactive R1 reagent or the like is separated to a holder 82b of a rotatable table 82a of the secondary reaction section 82. The conveyance catcher section 110 includes a motor 110a, a pulley 110b connected to the motor 110a, a pulley 110c arranged with a predetermined spacing from the pulley 110b, a drive transmission belt 110d attached to the pulley 110b and the pulley 110c, an arm 110e attached to the pulley 110c by way of a shaft, and a drive part 110f for moving the arm 110e in the up and down direction (Z-direction). A chuck part 110g for sandwiching and gripping the cuvette 6 is arranged at the distal end of the arm 110e.

The secondary reaction section 82 (FIG. 1) has a configuration similar to the primary reaction section 81, and is arranged to rotatably transport the cuvette 6 held at the holder 82b of the rotatable table 82a by a predetermined angle for every predetermined period (18 seconds in the present embodiment), and to stir the sample, the R1 reagent, the R2 reagent, the R3 reagent, and the R5 reagent in the cuvette 6. The secondary reaction section 82 is configured by the rotatable table 82a for conveying the cuvette 6 containing the sample, the R1 reagent, the R2 reagent, the R3 reagent and the R5 reagent in the rotating direction, and a conveyance mechanism section 82c for stirring the sample, the R1 reagent, the R2 reagent, the R3 reagent and the R5 reagent in the cuvette 6 and conveying the cuvette 6 containing the stirred sample and the like to the BF separator 102 to be hereinafter described. The conveyance mechanism section 82c has a function of again conveying the cuvette 6 processed by the BF separator 102 to the holder 82b of the rotatable table 82a.

The reagent dispensing arm 93 (see FIG. 1) has a function of aspirating the R3 reagent in the reagent bin 9 installed at the installing section 61a of the reagent installing section 61 and dispensing the aspirated R3 reagent into the cuvette 6 dispensed with the sample, the R1 reagent, and the R2 reagent of the secondary reaction section 82. The reagent dispensing arm 93 includes a motor 93a, a drive transmitting part 93b connected to the motor 93a, and an arm 93d attached to the drive transmitting part 93b by way of a shaft 93c. The drive transmitting part 93b is configured so as to turn the arm 93d by the driving force from the motor 93a with the shaft 93c as the center, and move the arm in the up and down direction (Z-direction). A nozzle 93e for aspirating and discharging the R3 reagent in the reagent bin 9 is attached to the distal end of the arm 93d. That is, the nozzle 93e aspirates the R3 reagent in the reagent bin 9 by way of the groove 61e of the upper surface 61b of the reagent installing section 61, and thereafter, dispenses the aspirated R3 reagent into the cuvette 6 dispensed with the sample, the R1 reagent, and the R2 reagent.

The BF separator 102 (see FIG. 1) has a configuration similar to the BF separator 101, and is arranged to remove the non-reactive R3 reagent in the cuvette 6 (see FIG. 16) received from the conveyance mechanism section 82c of the secondary reaction section 82. The BF separator 102 includes an installing section 102a for installing the cuvette 6 and conveying the cuvette 6 in the rotating direction, and a separation stirring section 102b for aspirating the non-reactive R3 reagent. The installing section 102a includes three installing holes 102c for holding the cuvette 6, and a magnet 102d respectively arranged at the side of the three installing holes 102c. Thus, the bound magnetic particles, the antigen, and the trapped antibody in the cuvette 6 installed in the installing hole 102c can be attracted to the magnet 102d side. The sample or the like in the cuvette 6 is aspirated with the separation stirring section 102b in the attracted state to remove the non-reactive (free) R3 reagent.

The reagent dispensing arm 94 (see FIG. 1) has a function of dispensing the R5 reagent containing luminescent substrate in the reagent bin (not shown) installed at the lower part of the immune analyzer 1 into the cuvette 6 containing the sample, the R1 reagent, and the R2 reagent, and the R3 reagent of the secondary reaction section 82. The reagent dispensing arm 94 includes a motor 94a, a drive transmitting part 94b connected to the motor 94a, and an arm 94c attached to the drive transmitting part 94b by way of a shaft. The drive transmitting part 94b is configured so as to turn the arm 94c by the driving force from the motor 94a with the shaft as the center, and move the arm in the up and down direction (Z-direction). A nozzle (not shown) for aspirating and discharging the R5 reagent is attached to the distal end of the arm 94c.

The first detector 120 (see FIG. 1) is arranged to measure the amount of antigen contained in a sample by acquiring the light generated in the reaction process of the labeled antibody bound to the antigen of the sample performed with a predetermined process and the luminescent substrate with a photo multiplier tube. The first detector 120 is configured by an installing section 121 for installing the cuvette 6 containing the sample, the R1 reagent, the R2 reagent, the R3 reagent, and the R5 reagent, and a conveyance mechanism section 122 for conveying the cuvette 6 (see FIG. 16) held at the holder 82b of the rotatable table 82a of the secondary reaction section 82.

The waste section 130 (see FIG. 1) is arranged to discard the measured sample measured by the first detector 120 and the cuvette 6 (see FIG. 16) containing the relevant sample. The waste section 130 is configured by an aspirating section 131 for aspirating the sample and various reagents in the cuvette 6 and a discarding hole 132 arranged at a position of a predetermined spacing from the aspirating section 131. After the measured sample and the like are aspirated by the aspirating section 131, the used cuvette 6 is discarded to a dust box (not shown) arranged at the lower part of the immune analyzer 1 by way of the discarding hole 132.

Figure 18:
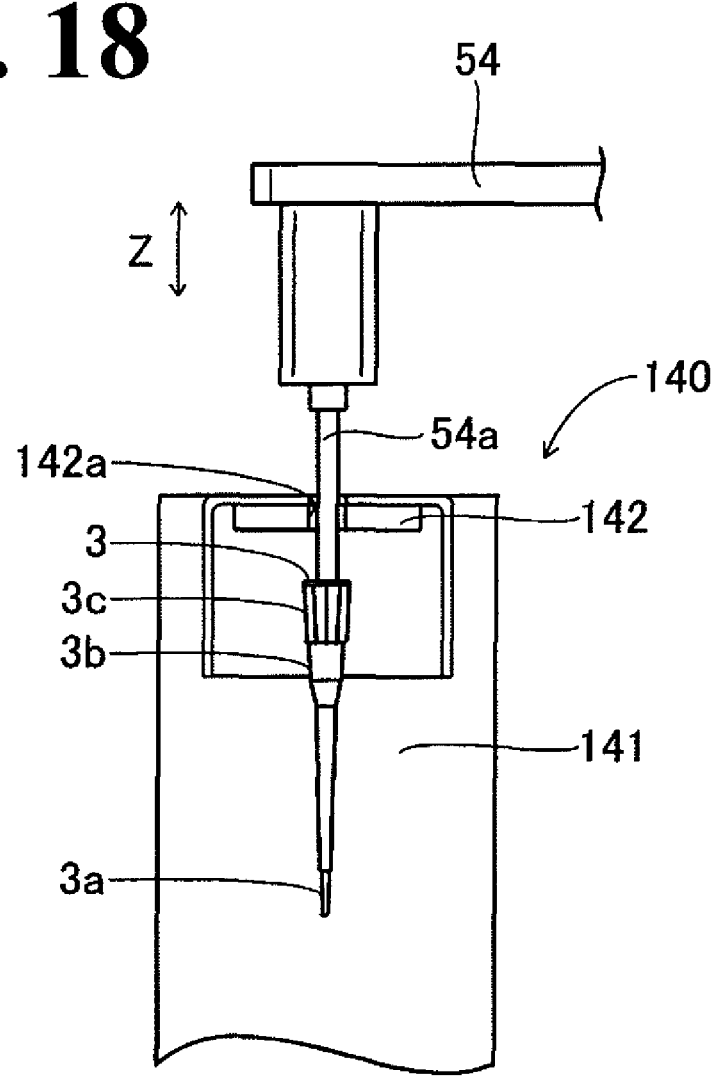
FIG. 18 is a side view showing a state in which the pipette tip is attached to the sample dispensing arm of the immune analyzer shown in FIG. 1.
Figure 19:
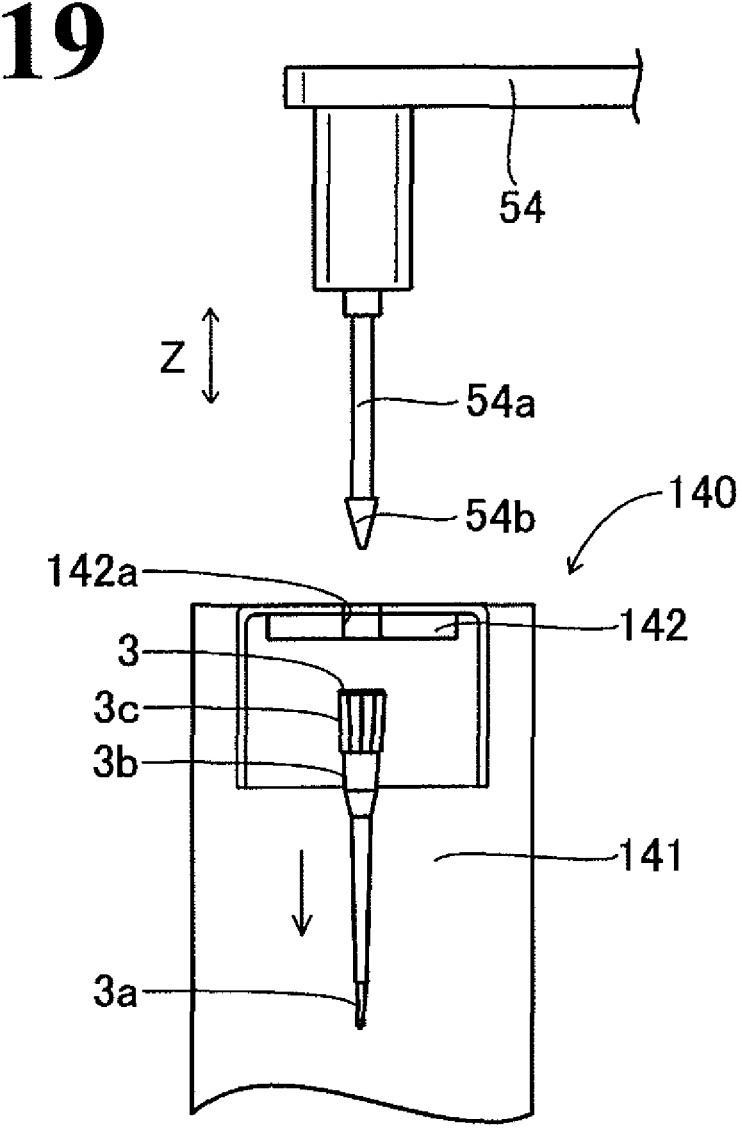
FIG. 19 is a side view showing a state in which the pipette tip is detached from the sample dispensing arm of the immune analyzer shown in FIG. 1.

The tip detachment section 140 (see FIG. 1) is provided to detach the pipette tip 3 attached to the sample dispensing arm 50. As shown in FIG. 18, the tip detachment section 140 includes a steel plate 141 arranged to extend in a vertical direction (Z-direction), and a release piece 142 made of resin attached to the steep plate 141. The release piece 142 is formed with a cutout 142a having a diameter smaller than the diameter of the attachment part 3c (see FIG. 19) of the pipette tip 3, and larger than the diameter of the distal end 54b (see FIG. 19) of the arm 54 of the sample dispensing arm 50.

Figure 20:
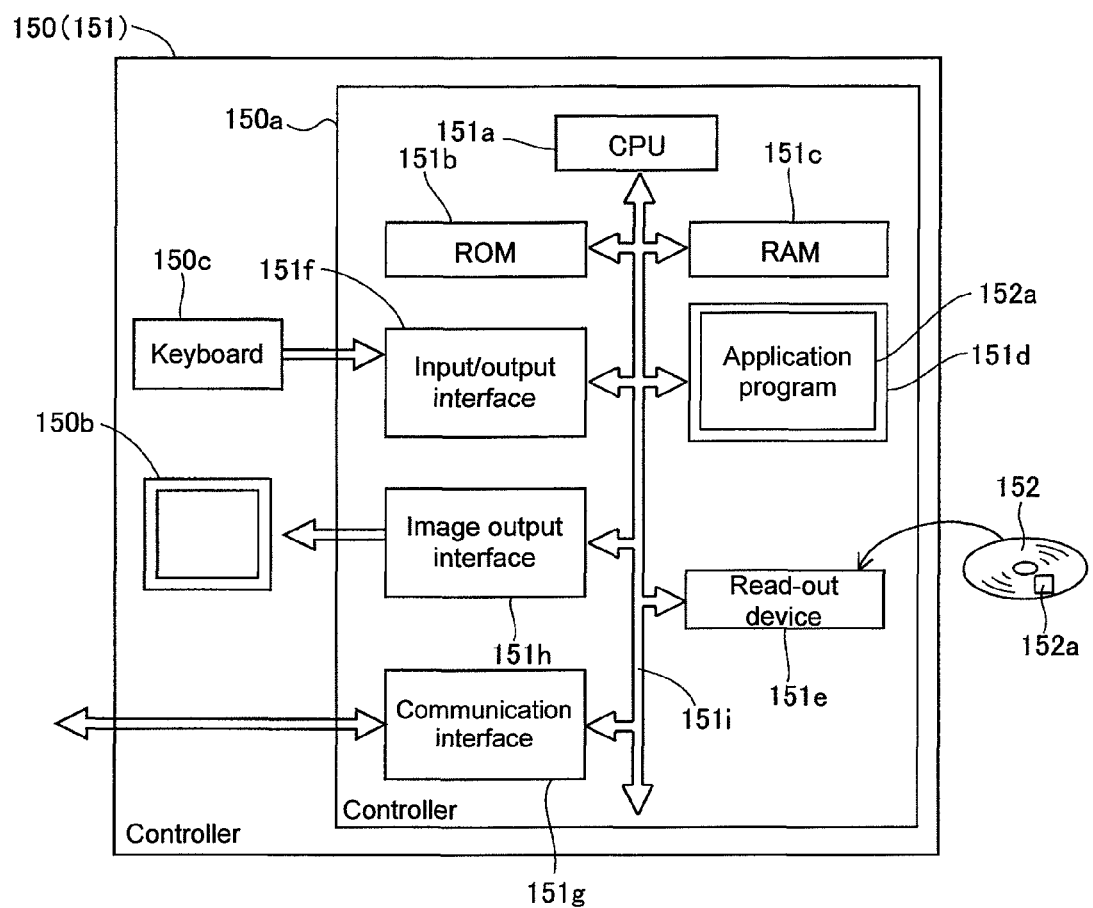
FIG. 20 is a block diagram showing a configuration of a data processing unit of the immune analyzer shown in FIG. 1.

The data processing unit 150 (see FIG. 1) is configured by a personal computer (PC), and includes a controller 150a (see FIG. 20) consisting of CPU, ROM, RAM, and the like, a display section 150b (see FIGS. 1 and 20), and a keyboard 150c (see FIGS. 1 and 20). The display section 150b is provided to display the analysis result obtained by analyzing data of the digital signal transmitted from the measurement unit 2.

The configuration of the control device 150 will now be described. As shown in FIG. 20, the data processing unit 150 is configured by a computer 151 mainly configured by the controller 150a, the display section 150b, and the keyboard 150c. The controller 150a is mainly configured by a CPU 151a, a ROM 151b, a RAM 151c, a hard disc 151d, a read-out device 151e, an input/output interface 151f, a communication interface 151g, and an image output interface 151h. The CPU 151a, the ROM 151b, the RAM 151c, the hard disc 151d, the read-out device 151e, the input/output interface 151f, the communication interface 151g, and the image output interface 151h are connected by a bus 151i.

The CPU 151a executes computer programs stored in the ROM 151b and the computer programs loaded in the RAM 151c. The computer 151 serves as the data processing unit 150 when the CPU 151a executes the application program 152a, as hereinafter described.

The ROM 151b is configured by mask ROM, PROM, EPROM, EEPROM, and the like, and is recorded with computer programs to be executed by the CPU 151a, data used for the same, and the like.

The RAM 151c is configured by SRAM, DRAM, and the like. The RAM 151c is used to read out the computer programs recorded on the ROM 151b and the hard disc 151d. The RAM 151c is used as a work region of the CPU 151a when executing the computer programs.

The hard disc 151d is installed with various computer programs to be executed by the CPU 151a such as operating system and application program, as well as data used in executing the computer program. The application program 152a for immune analysis according to the present embodiment is also installed in the hard disc 151d.

The read-out device 151e is configured by flexible disc drive, CD-ROM drive, DVD-ROM drive, and the like, and is able to read out computer programs and data recorded on a portable recording medium 152. The application program 152a for immune analysis is stored in the portable recording medium 152, wherein the computer 151 can read out the application program 152a from the portable recording medium 152, and can install the application program 152a to the hard disc 151d.

The application program 152a is not only provided by the portable recording medium 152, but is also provided by communication line (wired or wireless) from external devices communicatively connected with the computer 151 by way of the communication line. For instance, the application program 152a may be stored in the hard disc of the server computer on the Internet, so that the computer 151 can access the server computer 151 to download the application program 152a and install the application program 152a to the hard disc 151d.

Operating system providing graphical user interface environment such as Windows (registered trademark) manufactured and sold by US Microsoft Co. is installed in the hard disc 151d. In the following description, the application program 152a according to the present embodiment is assumed to operate on the operating system.

The input/output interface 151f is configured by serial interface such as USB, IEEE1394, RS-232C; parallel interface such as SCSI, IDE, IEEE1284; analog interface such as D/A converter, A/D converter, and the like. The keyboard 150c is connected to the input/output interface 151f, so that the user can input data to the computer 151 by using the keyboard 150c.

The communication interface 151g is, for example, Ethernet (registered trademark) interface. The computer 151 can transmit and receive data with the measurement unit 2 by using a predetermined communication protocol by means of the communication interface 151g.

The image output interface 151h is connected to the display section 150b configured by LCD, CRT, or the like, and is configured to output an image signal corresponding to the image data provided from the CPU 151a to the display section 150b. The display section 150b displays the image (screen) according to the input image signal. The display section 150b is configured to display buttons for making various instructions to the apparatus, wherein the apparatus performs the process corresponding to the button when the button is selected. In the display section 150b, the user can perform operations such as instruction to start or stop the measurement with respect to the apparatus, setting of the apparatus, and instruction to replace or take out reagent. The display section 150b is configured by a touch panel, so that the user can select the button by directly touching the button displayed on the display section 150b. The button can be selected by a pointer movable by a mouse or the like (not shown).

The immune analysis application program 152a installed in the hard disc 151d of the controller 150a measures the amount of antigen or antibody in the measurement specimen by using the light emission amount (data of digital signal) of the measurement specimen transmitted from the measurement unit 2.

Figure 21:
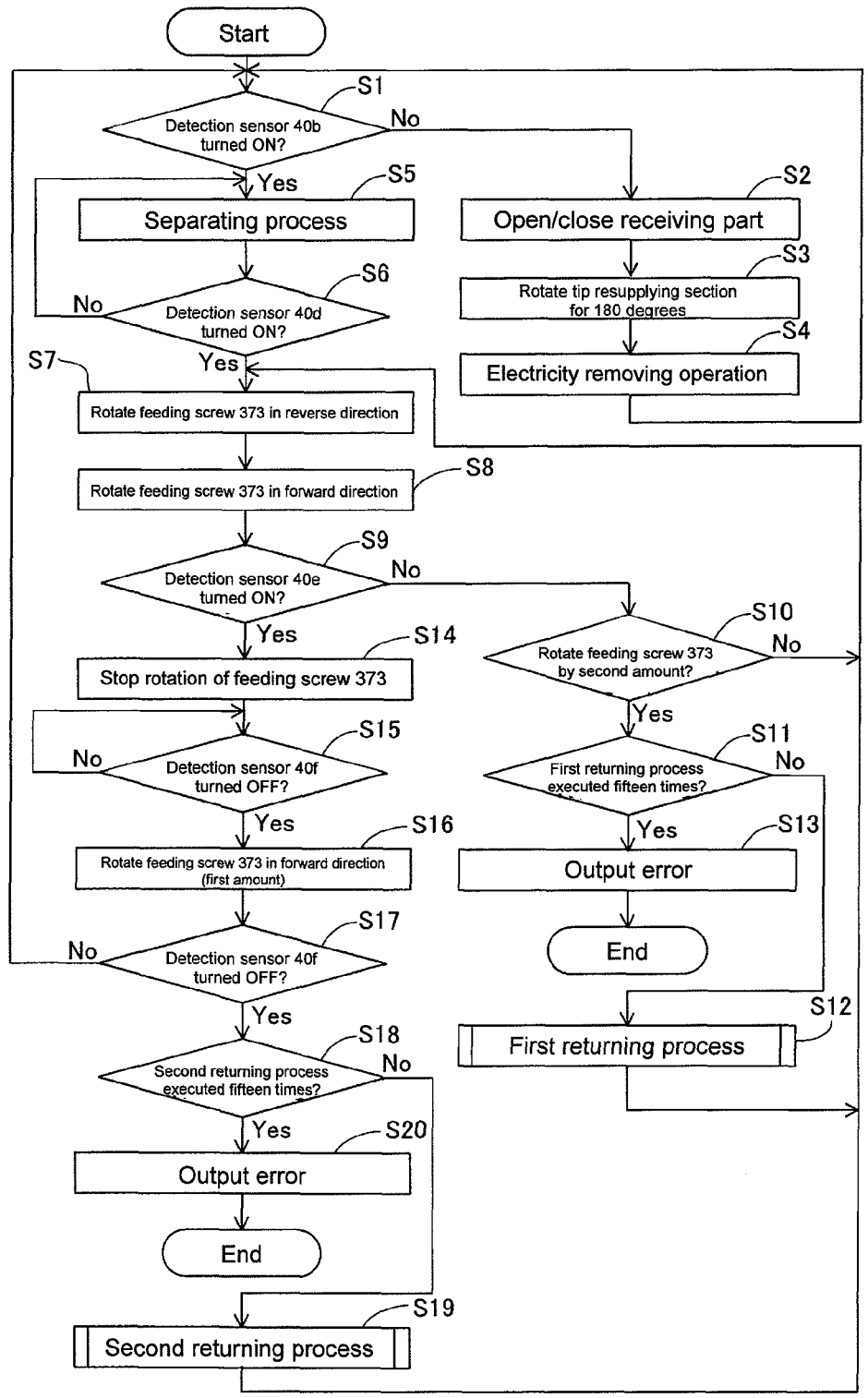
FIG. 21 is a flowchart describing a process flow of supplying the pipette tip contained in the tip resupplying section of the pipette tip supplier of immune analyzer shown in FIG. 1 to the transporting section.

FIG. 21 is a flowchart describing a process flow of a case of supplying the pipette tip contained in the tip resupplying section of the pipette tip supplier according to one embodiment of the present invention to the transporting section. The supplying operation of the pipette tip with respect to the transporting section of the pipette tip supplier will be described with reference to FIGS. 3, 8 to 10, 14, 15 and 21.

Whether or not the detection sensor 40b (see FIG. 9) is turned ON is firstly determined by the controller 2a (see FIG. 3) in step S1. Specifically, as shown in FIG. 8, whether or not the pipette tip 3 is stored in the tip storing section 34, that is, whether or not the pipette tip 3 is placed on the inclined surface 362 of the cutout mechanism part 361 is determined. As shown in FIG. 21, if determined that the detection sensor 40b (see FIG. 9) is not turned ON in step S1, the controller 2a determines that the pipette tip 3 is not stored in the tip storing section 34, and the process proceeds to step S2, the receiving part 351 is opened/closed between the position of I and the position of H in step S2, and the process proceeds to step S3. Thereafter, the drum 323 (see FIG. 10) of the tip resupplying section 31 is rotated 180 degrees in step S3, the eliminating operation of the static eliminator fan 33 is started at the same time as the rotating operation of the drum 323 of the tip resupplying section 31 in step S4, and the process returns to step S1. If determined that the detection sensor 40b is turned ON in step S1, the process proceeds to step S5, the separating process of the pipette tip 3 is carried out in step S5, the pipette tip 3 separated one by one is moved to the first transporting section 37, and then the process proceeds to step S6.

Subsequently, in step S6, whether or not the detection sensor 40d is turned ON is determined by the controller 2a. Specifically, whether or not the pipette tip 3 is moved from the inclined surface 364 of the cutout mechanism part 363 to the first transporting section 37 is determined. If determined that the detection sensor 40d is not turned ON in step S6, the process proceeds to step S5. If determined that the detection sensor 40d is turned ON in step S6, the process proceeds to step S7, and the feeding screw 373 is rotated in the reverse direction (direction of arrow X2) (see FIGS. 14 and 15) by a first amount (about 10 mm) in step S7. The distal end 3a of the pipette tip 3 becomes difficult to fit between the screws of the feeding screw 373. As a result, the attachment part 3c of the pipette tip 3 engages the feeding screw 373, and the pipette tip 3 can be held by the feeding screw 373 and the shaft 374.

Thereafter, in step S8, the feeding screw 373 is rotated in the forward direction so that the pipette tip 3 is transported in the direction of the arrow X1 (see FIG. 14), and the process proceeds to step S9. In the present embodiment, whether or not the detection sensor 40e (see FIG. 9) is turned ON is determined by the controller 2a in step S9. Specifically, whether or not the pipette tip 3 held between the feeding screw 373 (see FIG. 14) and the shaft 374 (see FIG. 14) is positioned at the suspended position in the vicinity of the insertion part 37a (see FIG. 14) is determined. If determined that the detection sensor 40e is not turned ON in step S9, the process proceeds to step S10, and whether or not the feeding screw 373 is rotated by a second amount (about 100 mm) is determined in step S10. That is, whether or not the feeding screw 373 is rotated by the entire length (about 100 mm) of the feeding screw 373, and the pipette tip 3 is moved to the suspended position in the vicinity of the insertion part 37a are determined. If determined that the feeding screw 373 is not rotated by the second amount (about 100 mm) in step S10, the process returns to step S8. If determined that the feeding screw 373 is rotated by the second amount (about 100 mm) in step S10, the process proceeds to step S11.

Whether or not the first returning process to be hereinafter described is executed over the second number of times N2 (fifteen times) by the controller 2a is then determined in step S11. If determined that the first returning process is not executed over the second number of times N2 (fifteen times) in step S11, the process proceeds to step S12, the first returning process is executed in step S12, and the process then returns to step S7. The details of the first returning process of step S12 will be hereinafter described. If determined that the first returning process is executed over the second number of times N2 (fifteen times) in step S11, the process proceeds to step S13, and the error output is executed by the controller 2a in step S13. Thereafter, the supplying operation of the pipette tip 3 with respect to the transporting section 38 of the pipette tip supplier 30 is terminated.

If determined that the detection sensor 40e is turned ON by the controller 2a in step S9, the process proceeds to step S14, the rotation of the feeding screw 373 is stopped in step S14, and the process proceeds to step S15. In other words, the transportation in the forward direction (direction of arrow X1) of the pipette tip 3 is stopped at the suspended position before arriving at the insertion part 37a. The suspended position is a position of about 10 mm from the insertion part 37a in the direction of the arrow X2.

Whether or not the detection sensor 40f is not turned OFF is determined in step S15 by the controller 2a. In other words, whether or not the pipette tip 3 is positioned at the position below the shoot 39a of the second transporting section 38 is determined. If determined that the detection sensor 40f is not turned OFF in step S15, the operation of step S15 is repeated. If determined that the detection sensor 40f is turned OFF, the process proceeds to step S16. Thereafter, the feeding screw 373 is rotated by the first amount (about 10 mm) in the forward direction so that the pipette tip 3 is transported in the direction of the arrow X1 (see FIG. 14) in step S16, and the process proceeds to step S17. In other words, the pipette tip 3 is transported to the insertion part 37a from the suspended position before arriving at the insertion part 37a of the first transporting section 37 by the controller 2a.

Whether or not the detection sensor 40f is turned OFF is then determined by the controller 2a in step S17. Specifically, whether or not the pipette tip 3 held at the first transporting section 37 is still positioned at the first transporting section 37 without being dropped on the second transporting section 38 by way of the shoot 39a by the insertion part 37a is determined. If determined that the detection sensor 40f is not turned OFF (turned ON) in step S17, the pipette tip 3 is dropped in the second transporting section 38, and thus the process returns to step S1. If determined that the detection sensor 40f is turned OFF in step S17, the process proceeds to step S18.

Whether or not the second returning process to be hereinafter described is executed over the fourth number of times N4 (fifteen times) by the controller 2a is determined in step S18. If determined that the second returning process is not executed over the fourth number of times N4 (fifteen times) in step S18, the process proceeds to step S19, the second returning process is executed in step S19, and the process returns to step S7. The details of the second returning process of step S19 will be hereinafter described. If determined that the second returning process is executed over the fourth number of times N4 (fifteen times) in step S18, the process proceeds to step S20, and the error output is executed by the controller 2a in step S20. Thereafter, the supplying operation of the pipette tip 3 with respect to the second transporting section 38 of the pipette tip supplier 30 is terminated.

Figure 22:
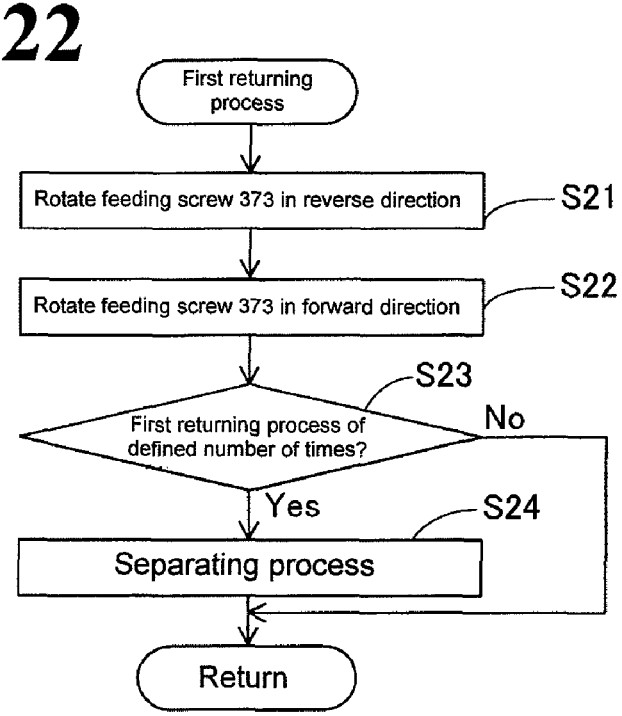
FIG. 22 is a flowchart describing the details of a first returning process executed in the flowchart shown in FIG. 21.

FIG. 22 is a flowchart describing the details of the first returning process executed in the flowchart shown in FIG. 21. The details of the first returning process of the pipette tip 3 in the pipette tip supplier 30 will be described with reference to FIGS. 3, 14, 15, and 22.

As shown in FIG. 22, in the first returning process, the feeding screw 373 is rotated by the first amount (about 10 mm) in the reverse direction (direction of arrow X2) (see FIGS. 14 and 15) in step S21, the feeding screw 373 is then rotated by the first amount in the forward direction (direction of arrow X1) (see FIGS. 14 and 15) in step S22, and the process proceeds to step S23. The distal end 3a of the pipette tip 3 is likely to fit between the screws of the feeding screws 373. As a result, the attachment part 3c of the pipette tip 3 engages the feeding screw 373, and the pipette tip 3 can be normally held by the feeding screw 373 and the shaft 374. The pipette tip caught at the feeding screw 373 or the shaft 374 and not dropped now can be expected to be dropped. Whether or not the first returning process of the defined number of times (first number of times N1: fourth time and eighth time) is determined by the controller 2a (see FIG. 3) in step S23. If determined as the first returning process of the defined number of times in step S23, the process proceeds to step S24, the separating process of the pipette tip 3 is performed in step S24, the pipette tip 3 separated one by one is moved to the first transporting section 37, and the first returning process is terminated. If determined as not the first returning process of the defined number of times (first number of times N1: fourth time and eighth time) in step S23, the first returning process is terminated. In other words, in the first returning process of the fourth time and eighth time, the new pipette tip 3 is supplied to the first transporting section 37 by performing the separating process of the pipette tip 3. The newly supplied pipette tip 3 may contact the pipette tip 3 not arranged in the first transporting section 37 with the attachment port facing upward, and an external force for changing the orientation of the pipette tip 3 so as to be arranged in the transporting section with the attachment port facing upward can be applied on the pipette tip 3.

Figure 23:
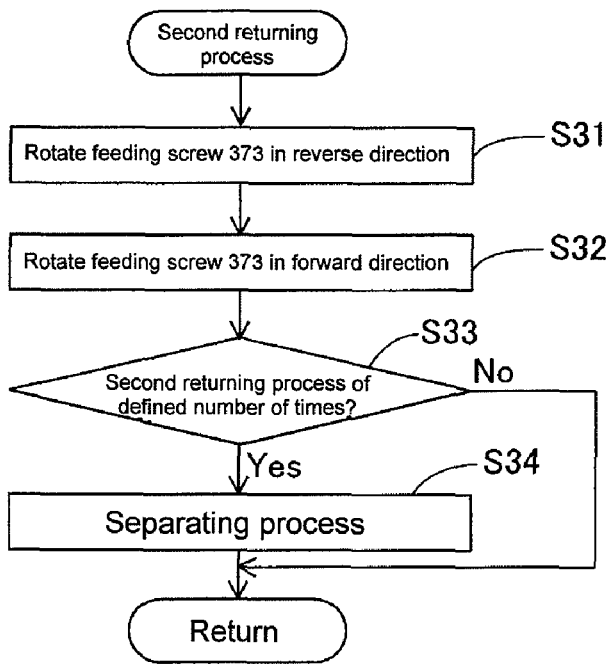
FIG. 23 is a flowchart describing the details of a second returning process executed in the flowchart shown in FIG. 21.

FIG. 23 is a flowchart describing the details of the second returning process executed in the flowchart shown in FIG. 21. The details of the second returning process of the pipette tip 3 in the pipette tip supplier 30 will be described with reference to FIGS. 3, 14, 15, and 23.

As shown in FIG. 23, the feeding screw 373 is rotated by the first amount (about 10 mm) in the forward direction (direction of arrow X1) (see FIGS. 14 and 15) in step S31, the feeding screw 373 is then rotated by the first amount in the reverse direction (direction of arrow X2) (see FIGS. 14 and 15) in step S32, and the process proceeds to step S33. The distal end 3a of the pipette tip 3 is likely to fit between the screws of the feeding screws 373. As a result, the attachment part 3c of the pipette tip 3 engages the feeding screw 373, and the pipette tip 3 can be normally held by the feeding screw 373 and the shaft 374. Whether or not the second returning process of the defined number of times (third number of times N3: fifth time and tenth time) is determined by the controller 2a (see FIG. 3) in step S33. If determined as the second returning process of the defined number of times in step S33, the process proceeds to step S34, the separating process of the pipette tip 3 is performed in step S34, the pipette tip 3 separated one by one is moved to the first transporting section 37, and the second returning process is terminated. If determined as not the second returning process of the defined number of times (third number of times N3: fifth time and tenth time) in step S33, the second returning process is terminated. In other words, in the second returning process of the fifth time and tenth time, the new pipette tip 3 is supplied to the first transporting section 37 by performing the separating process of the pipette tip 3. The newly supplied pipette tip 3 may contact the pipette tip 3 not arranged in the first transporting section 37 with the attachment port facing upward, and an external force for changing the orientation of the pipette tip 3 so as to be arranged in the transporting section with the attachment port facing upward can be applied on the pipette tip 3.

In the present embodiment, the first transporting section 37 for dropping the transported pipette tip 3 in the inserting part 37a and the controller 2a for controlling the first transporting section 37 so as to stop the transporting operation when the pipette tip 3 is detected at the suspended position before arriving at the insertion part 37a by the detection sensor 40e are arranged. The pipette tip 3 previously dropped from the insertion part 37a then can be moved in the direction of the arrow Y1 from the dropped point by the feeding screw 385 of the first transporting section 37 while the transporting operation is stopped. Thus, even if the pipette tip 3 is newly dropped from the insertion part 37a of the first transporting section 37, the pipette tips 3 will not be clogged near the dropped point or arranged at the dropped point in an overlapping state, and the pipette tips 3 can be smoothly conveyed.

In the present embodiment, after performing the transporting operation by the second amount (about 100 mm) in the transporting direction (direction of arrow X1) of the pipette tip 3 by the first transporting section 37 with the pipette tip 3 detected by the detection sensor 40d, the controller 2a alternately executes the reverse transport control in which the feeding screw 373 of the first transporting section 37 is transport operated in the reverse direction (direction of arrow X2) of the transporting direction of the pipette tip 3 when the pipette tip 3 is not detected at the suspended position before arriving at the insertion part 37a by the detection sensor 40e; and the forward transport control in which the feeding screw 373 of the first transporting section 37 is transport operated in the transporting direction (direction of arrow X1). The external force for changing the orientation of the pipette tip 3 so as to be arranged in the feeding screw 373 of the first transporting section 37 with the attachment part 3c facing upward can be applied on the pipette tip 3 with respect to the pipette tip 3 arranged in the first transporting section 37 in an unstable state without being arranged with the attachment part 3c facing upward in the feeding screw 373 of the first transporting section 37.

In the present embodiment, if the detection sensor 40e does not detect the pipette tip 3, the reverse transport control in which the feeding screw 373 of the first transporting section 37 is transport operated in the reverse direction (direction of arrow X2) of the transporting direction of the pipette tip 3, and the forward transport control in which the feeding screw 373 of the first transporting section 37 is transport operated in the transporting direction (direction of arrow X1) are repeated for the first number of times N1 (four times and eight times), and thereafter, the separating operation of separating the pipette tips 3 is executed, and the separating mechanism section 36 is controlled by the controller 2a so as to supply the separated pipette tip 3 to the first transporting section 37. As a result of alternately executing the reverse transport control and the forward transport control, the pipette tip 3 newly supplied to the first transporting section 37 contacts the pipette tip 3 not arranged on the feeding screw 373 of the first transporting section 37 with the attachment part 3c facing upward, and the external force for changing the orientation of the pipette tip 3 arranged in the first transporting section 37 in an unstable state can be applied to the pipette tip 3.

In the present embodiment, the controller 2a is configured to repeat the reverse transport control of operating the feeding screw 373 of the first transporting section 37 in the reverse direction (direction of arrow X2) to the transporting direction of the pipette tip 3 and the forward transport control of operating the feeding screw 373 of the first transporting section 37 in the transporting direction (direction of arrow X1) for the second number of times (fifteen times), and thereafter, output error if the detection sensor 40e does not detect the pipette tip 3 at the suspended position. Accordingly, the user can be notified of the occurrence of abnormality if the orientation of the pipette tip 3 is not the normal orientation even if the orientation returning operation of the pipette tip 3 is repeatedly performed.

In the present embodiment, the controller 2a is configured to resume the transporting operation of the feeding screw 373 of the first transporting section 37, in which transporting operation is stopped, when the pipette tip 3 is not detected by the detection sensor 40f, and transport the pipette tip 3 to the insertion part 37a and drop the same. The pipette tips 3 are thus suppressed from being clogged or arranged in an overlapping manner at the dropped point of the second transporting section 38 below the insertion part 37a.

In the present embodiment, after resuming the transporting operation of the feeding screw 373 of the first transporting section 37 in which transporting operation is stopped, and transporting the pipette tip 3 to the insertion part 37a, and dropping the same, the controller 2a alternately executes the forward transport control of transport operating the feeding screw 373 of the first transporting section 37 in the transporting direction (direction of arrow X1) of the pipette tip 3 and the reverse transport control of transport operating the feeding screw 373 of the first transporting direction 37 in the reverse direction (direction of arrow X2) to the transporting direction when the pipette tip 3 is not detected by the detection sensor 40f. The outer force for changing the orientation of the pipette tip 3 arranged at the feeding screw 373 of the first transporting section 37 in an unstable state without being dropped from the insertion part 37a of the feeding screw 373 of the first transporting section 37 can be applied to the pipette tip 3.

In the present embodiment, the controller 2a is configured to repeat the forward transport control of operating the feeding screw 373 of the first transporting section 37 in the transporting direction (direction of arrow X1) and the reverse transport control of operating the feeding screw 373 of the first transporting section 37 in the reverse direction (direction of arrow X2) to the transporting direction of the pipette tip 3 for the fourth number of times (fifteen times), and thereafter, output error if the detection sensor 40f does not detect that the pipette tip 3 is dropped to the second transporting section 38. Accordingly, the user can be notified of the occurrence of abnormality if the orientation of the pipette tip 3 is not the normal orientation even if the orientation returning operation of the pipette tip 3 is repeatedly performed.

The embodiment disclosed herein is merely illustrative in all aspects and should not be recognized as being restrictive. The scope of the invention is defined by the scope of the claims rather than the description of the above-described embodiment, and meaning equivalent to the claims and all modifications within the scope are encompassed herein.

For instance, in the present embodiment, an example of applying the pipette tip supplier for supplying disposable pipette tips one by one to the immune analyzer has been shown, but the present invention is not limited thereto. As long as being apparatus using disposable pipette tips, the pipette tip supplier can be applied to apparatuses other than the immune analyzer, such as gene amplification measurement apparatus, blood coagulation measurement apparatus, and multiple blood cell analyzer.

In the present embodiment, an example is described wherein the forward transport control and the reverse transport control of the feeding screw 373 of the first transporting section 37 are repeated over the first number of times (four times and eight times), and thereafter, the separating operation of separating the pipette tips is executed in the separating mechanism section and the control is performed by the controller so that the pipette tip is supplied to the first transporting section 37, but the present invention is not limited thereto. After the forward transport control and the reverse transport control of the feeding screw 373 of the first transporting section 37 are repeated other than the first number of times (four times or eight times), the separating operation of separating the pipette tips may be executed in the separating mechanism section and control may be performed by the controller so that the pipette tip is supplied to the first transporting section 37.

Furthermore, in the above-described embodiment, an example is described wherein, after the forward transport control and the reverse transport control of the feeding screw 373 of the first transporting section 37 are repeated over the second number of times (fifteen times), the control is performed to output error by the controller when the pipette tip is not detected at the inserting part by the projection sensor 40e, but the present invention is not limited thereto. The forward transport control and the reverse transport control of the feeding screw 373 of the first transporting section 37 may be repeated over the number of times other than fifteen times, and thereafter the control may be performed to output error by the controller when the pipette tip is not detected at the inserting part by the projection sensor 40e.

In the present embodiment, an example is described wherein the forward transport control and the reverse transport control of the feeding screw 373 of the first transporting section 37 are repeated over the third number of times (five times and ten times), and thereafter, the separating operation of separating the pipette tips is executed in the separating mechanism section and the control is performed by the controller so that the pipette tip is supplied to the first transporting section 37, but the present invention is not limited thereto. After the forward transport control and the reverse transport control of the feeding screw 373 of the first transporting section 37 are repeated other than the third number of times (five times or ten times), the separating operation of separating the pipette tips may be executed in the separating mechanism section and control may be performed by the controller so that the pipette tip is supplied to the first transporting section 37.

Furthermore, in the above-described embodiment, an example is described wherein, after the forward transport control and the reverse transport control of the feeding screw 373 of the first transporting section 37 are repeated fifteen times, being the fourth number of times, the control is performed to output error by the controller when the pipette tip is not detected at the inserting part by the projection sensor 40f, but the present invention is not limited thereto. The forward transport control and the reverse transport control of the feeding screw 373 of the first transporting section 37 may be repeated over the number of times other than fifteen times, and thereafter the control may be performed to output error by the controller when the pipette tip is not detected at the inserting part by the projection sensor 40f.

What is claimed is:

1. A pipette tip supplier for supplying a pipette tip used in a dispensing device, comprising:
    a plurality of pipette tips;
    a container for configured to contain the pipette tips;
    a separator for configured to separate the pipette tips supplied from the container one by one;
    a first transporting section configured to transport the pipette tips separated by the separator to a insertion part position via a suspended position and configured to drop the pipette tips from the insertion part position, wherein a first pipette is transported first followed by a second pipette tip;
    a first detector configured to detect a second pipette tip at the suspended position before the second pipette tip arrives at the insertion part position;
    a second transporting section configured to receive, at a receiving position, the pipette tip dropped from the first transporting section through the insertion part position, and configured to transport the pipette tip;
    a second detector configured to detect the pipette tip at the receiving position; and
    a controller for controlling configured to control, responsive to a detection of the second pipette tip by the first detector, the first transporting section so as to suspend transporting operation of the second pipette tip, and configured to control the first transporting section so as to resume the suspended transporting operation of the second pipette tip when the second detector does not detect the first pipette tip at the receiving position;
    the controller is further configured to execute a reverse transport control for controlling the first transporting section so as to transport the second pipette tip in a direction opposite to a transporting direction of the first transporting section and a forward transport control for controlling the first transporting section so as to transport the second pipette tip in the transporting direction of the first transporting section, when the second pipette tip is not detected by the second detector after controlling the first transporting section so as to resume the suspended transporting operation to transport the second pipette tip to the insertion part position from the suspended position and drop the second pipette tip.

2. The pipette tip supplier of claim 1, wherein the controller is configured to execute a reverse transport control for controlling the first transporting section so as to transport the first pipette tip in a direction opposite to a transporting direction of the first transporting section and a forward transport control for controlling the transporting section so as to transport the first pipette tip in the transporting direction of the first transporting section, when the first pipette tip is not detected by the second detector after controlling the first transporting section so as to resume the suspended transporting operation to transport the first pipette tip to the dropping position from the suspended position and drop the first pipette tip.

3. The pipette tip supplier of claim 1, wherein the controller is configured to control the separator so as to separate the pipette tips supplied from the container and so as to supply a separated pipette tip to the transporting section after executing the reverse transport control and the forward transport control over a predetermined number of times.

4. The pipette tip supplier of claim 1, wherein the controller is configured to output error information indicating that an error is occurring, when the second pipette tip is not detected by the second detector after executing the reverse transport control and the forward transport control over the predetermined number of times.

5. The pipette tip supplier of claim 1, wherein
    each of the pipette tips contained in the container has an attachment part to be attached to the dispensing device at one end; and
    the first transporting section transports the pipette tips separated by the separator in a state that attachment parts of the pipette tips is facing upward.

6. The pipette tip supplier of claim 5, wherein the second transporting section is configured to hold a pipette tip dropped from the first transporting section in a state that attachment part of the pipette tip is facing upward.

7. The pipette tip supplier of claim 1, further comprising a third detector configured to detect whether or not a pipette tip separated by the separator is transported to the first transporting section.

8. The pipette tip supplier of claim 7, wherein the controller is further configured to execute a reverse transport control for controlling the first transporting section so as to transport the second pipette tip in a direction opposite to a transporting direction of the first transporting section and a forward transport control for controlling the first transporting section so as to transport the second pipette tip in the transporting direction of the first transporting section, when the second pipette tip is not detected at the suspended position by the first detector after controlling the first transporting section so as to transport the second pipette tip by a predetermined amount in the transporting direction of the transporting section in a state that a third detector detects the second pipette tip separated by the separator is transported to the first transporting section.

9. The pipette tip supplier of claim 8, wherein the controller is configured to control the separator so as to separate the pipette tips supplied from the container and so as to supply a separated pipette tip to the transporting section after executing the reverse transport control and the forward transport control over a predetermined number of times.

10. The pipette tip supplier of claim 8, wherein the controller is configured to output error information indicating that an error is occurring, when the second pipette tip is not detected at the suspended position by the first detector after executing the reverse transport control and the forward transport control over the predetermined number of times.

11. The pipette tip supplier of claim 1, wherein
    the first transporting section comprises a transport screw for transporting a pipette tip separated by the separator, and a supporting member for supporting the pipette tip between the transport screw and the supporting member; and
    the transport screw and the supporting member are arranged parallel to each other with a spacing substantially the same as an outer diameter of a body part of the pipette tip on an upper side of a center of gravity of the pipette tip.

12. The pipette tip supplier of claim 1, further comprising a static eliminator for performing an eliminating operation for eliminating electrification charge of the pipette tips supplied from the container.

13. A sample analyzer comprising:
the pipette tip supplier of claim 1;
a dispenser comprising an aspirating nozzle to which the pipette tip supplied by the pipette tip supplier is attachable, and for dispensing a sample with the pipette tip attached to the aspirating nozzle; and
an analyzing section for analyzing the sample dispensed by the dispenser.

14. A pipette tip supplying method for supplying a pipette tip used in a dispensing device, comprising steps of:
(a) separating pipette tips supplied from a container containing pipette tips one by one;
(b) transporting using a first transporting section a first pipette tip separated in step (a), one by one, toward an insertion part position through a suspended position;
(c) dropping the first pipette tip from the insertion part position on the first transporting section;
(d) receiving, at a receiving position on a second transporting section, the first pipette tip dropped through the insertion part position and transporting the received first pipette tip, the second transporting section having a second detector for detecting a pipette tip at the receiving position;
(e) detecting using a first detector a second pipette tip at the suspended position before the second pipette tip arrives at the insertion part position;
(f) when the second pipette tip is detected in step (e), suspending transporting operation of the second pipette tip; and
(g) resuming the suspending transporting operation of the second pipette tip to the receiving position when the second detector does not detect the first pipette tip at the receiving position;
(h) execute a reverse transport control for controlling the first transporting section so as to transport the second pipette tip in a direction opposite to a transporting direction of the first transporting section and a forward transport control for controlling the first transporting section so as to transport the second pipette tip in the transporting direction of the first transporting section, when the second pipette tip is not detected by the second detector after controlling the first transporting section so as to resume the suspended transporting operation and to transport the second pipette tip to the insertion part position from the suspended position and drop the second pipette tip.

* * * * *